US008128681B2

(12) United States Patent
Shoemaker et al.

(10) Patent No.: US 8,128,681 B2
(45) Date of Patent: Mar. 6, 2012

(54) VENOUS VALVE APPARATUS, SYSTEM, AND METHOD

(75) Inventors: Susan M. Shoemaker, Elk River, MN (US); Leonard B. Richardson, Minneapolis, MN (US); Paul F. Chouinard, Maple Grove, MN (US); Jason P. Hill, Cottage Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 979 days.

(21) Appl. No.: 10/741,992

(22) Filed: Dec. 19, 2003

(65) Prior Publication Data

US 2005/0137681 A1 Jun. 23, 2005

(51) Int. Cl.
*A61F 2/06* (2006.01)

(52) U.S. Cl. ............ 623/1.24; 623/1.25; 623/1.26; 623/2.16; 623/2.17; 623/2.18

(58) Field of Classification Search ............ 623/2.1, 623/1.24–1.26, 2.16–2.18
See application file for complete search history.

(56) References Cited

U.S. PATENT DOCUMENTS

| | | | | |
|---|---|---|---|---|
| 3,755,823 | A * | 9/1973 | Hancock | 623/2.18 |
| 4,343,048 | A * | 8/1982 | Ross et al. | 623/2.14 |
| 4,477,930 | A | 10/1984 | Totten et al. | |
| 4,759,759 | A * | 7/1988 | Walker et al. | 623/2.16 |
| 5,411,552 | A | 5/1995 | Andersen et al. | 623/2 |
| 5,469,868 | A | 11/1995 | Reger | 128/898 |
| 5,824,061 | A | 10/1998 | Quijano et al. | 623/2 |
| 5,840,081 | A * | 11/1998 | Andersen et al. | 623/1.11 |
| 5,855,601 | A * | 1/1999 | Bessler et al. | 623/2.38 |
| 6,027,525 | A | 2/2000 | Suh et al. | 623/1 |
| 6,162,245 | A | 12/2000 | Jayaraman | 623/1.15 |
| 6,221,091 | B1 | 4/2001 | Khosravi | |
| 6,241,763 | B1 | 6/2001 | Drasler et al. | 623/1.24 |
| 6,299,637 | B1 | 10/2001 | Shaolian et al. | 623/1.24 |
| 6,334,873 | B1 | 1/2002 | Lane et al. | 623/2.14 |
| 6,440,164 | B1 | 8/2002 | DiMatteo et al. | 623/1.24 |
| 6,454,799 | B1 * | 9/2002 | Schreck | 623/2.18 |

(Continued)

FOREIGN PATENT DOCUMENTS

WO WO 2004/019825 3/2004

(Continued)

OTHER PUBLICATIONS

US 6,673,110, 01/2004, Alfieri et al. (withdrawn)

(Continued)

*Primary Examiner* — Thomas J Sweet
*Assistant Examiner* — Christopher D Prone
(74) *Attorney, Agent, or Firm* — Vidas, Arrett & Steinkraus

(57) ABSTRACT

A venous valve with a tubular frame that includes an outer surface and an inner surface opposite the outer surface and defining a lumen, and a cover over at least the outer surface of the tubular frame, where the cover includes surfaces defining a reversibly sealable opening for unidirectional flow of a liquid through the lumen. A system with the venous valve and a catheter including a proximal end and a distal end, the venous valve located between the proximal end and distal end of the catheter. A method including forming the venous valve and reversibly joining the venous valve and a catheter. A method including positioning at least part of the catheter including the venous valve at a predetermined location and deploying the venous valve from the catheter at the predetermined location.

14 Claims, 16 Drawing Sheets

U.S. PATENT DOCUMENTS

| | | | | |
|---|---|---|---|---|
| 6,494,909 B2 | 12/2002 | Greenhalgh | | 623/1.24 |
| 6,503,272 B2 | 1/2003 | Duerig et al. | | 623/1.24 |
| 6,508,833 B2 | 1/2003 | Pavcnik et al. | | 623/1.15 |
| 6,527,800 B1 | 3/2003 | McGuckin, Jr. et al. | | 623/1.24 |
| 6,562,069 B2 | 5/2003 | Cai et al. | | 623/2.12 |
| 6,632,243 B1 | 10/2003 | Zadno-Azizi et al. | | 623/1.24 |
| 6,666,885 B2 | 12/2003 | Moe | | 623/2.12 |
| 6,666,886 B1 | 12/2003 | Tranquillo et al. | | 623/2.42 |
| 6,669,725 B2 | 12/2003 | Scott | | 623/2.36 |
| 6,673,109 B2 | 1/2004 | Cox | | 623/2.12 |
| 6,676,698 B2 | 1/2004 | McGuckin, Jr. et al. | | 623/1.24 |
| 6,676,702 B2 | 1/2004 | Mathis | | 623/2.36 |
| 6,682,558 B2 | 1/2004 | Tu et al. | | 623/2.11 |
| 6,682,559 B2 | 1/2004 | Myers et al. | | 623/2.13 |
| 6,685,739 B2 | 2/2004 | DiMatteo et al. | | 623/1.24 |
| 6,692,512 B2 | 2/2004 | Jang | | 606/200 |
| 6,695,866 B1 | 2/2004 | Kuehn et al. | | 606/213 |
| 6,695,878 B2 | 2/2004 | McGuckin, Jr. et al. | | 623/1.19 |
| 6,709,456 B2 | 3/2004 | Langberg et al. | | 623/2.37 |
| 6,709,457 B1 | 3/2004 | Otte et al. | | 623/2.4 |
| 6,716,241 B2 | 4/2004 | Wilder et al. | | 623/1.24 |
| 6,716,244 B2 | 4/2004 | Klaco | | 623/2.4 |
| 6,719,767 B1 | 4/2004 | Kimblad | | 606/151 |
| 6,719,784 B2 | 4/2004 | Henderson | | 623/1.44 |
| 6,719,786 B2 | 4/2004 | Ryan et al. | | 623/2.11 |
| 6,719,787 B2 | 4/2004 | Cox | | 623/2.12 |
| 6,719,788 B2 | 4/2004 | Cox | | 623/2.12 |
| 6,719,789 B2 | 4/2004 | Cox | | 623/2.13 |
| 6,719,790 B2 | 4/2004 | Brendzel et al. | | 623/2.4 |
| 6,723,038 B1 | 4/2004 | Schroeder et al. | | 600/16 |
| 6,723,122 B2 | 4/2004 | Yang et al. | | 623/2.1 |
| 6,723,123 B1 | 4/2004 | Kazatchkov et al. | | 623/2.2 |
| 6,726,715 B2 | 4/2004 | Sutherland | | 623/2.1 |
| 6,726,716 B2 | 4/2004 | Marquez | | 623/2.36 |
| 6,726,717 B2 | 4/2004 | Alfieri et al. | | 623/2.36 |
| 6,730,118 B2 | 5/2004 | Spenser et al. | | 623/1.24 |
| 6,730,121 B2 | 5/2004 | Ortiz et al. | | 623/2.17 |
| 6,730,122 B1 | 5/2004 | Pan et al. | | 623/2.33 |
| 6,736,845 B2 | 5/2004 | Marquez et al. | | 623/2.11 |
| 6,736,846 B2 | 5/2004 | Cox | | 623/2.12 |
| 6,749,630 B2 | 6/2004 | McCarthy et al. | | 623/2.36 |
| 6,752,813 B2 | 6/2004 | Goldfarb et al. | | 606/139 |
| 6,752,828 B2 | 6/2004 | Thornton | | 623/1.24 |
| 6,755,857 B2 | 6/2004 | Peterson et al. | | 623/2.17 |
| 6,761,734 B2 | 7/2004 | Suhr | | 623/1.35 |
| 6,761,735 B2 | 7/2004 | Eberhardt et al. | | 623/2.1 |
| 6,764,494 B2 | 7/2004 | Menz et al. | | 606/159 |
| 6,764,508 B1 | 7/2004 | Roehe et al. | | 623/2.11 |
| 6,764,509 B2 | 7/2004 | Chinn et al. | | 623/2.12 |
| 6,764,510 B2 | 7/2004 | Vidlund et al. | | 623/2.34 |
| 6,767,362 B2 | 7/2004 | Schreck | | 623/2.11 |
| 6,769,434 B2 | 8/2004 | Liddicoat et al. | | 128/898 |
| 6,770,083 B2 | 8/2004 | Seguin | | 606/142 |
| 6,780,200 B2 | 8/2004 | Jansen | | 623/2.17 |
| 6,786,924 B2 | 9/2004 | Ryan et al. | | 623/2.36 |
| 6,786,925 B1 | 9/2004 | Buchanan et al. | | 623/2.38 |
| 6,790,229 B1 | 9/2004 | Berreklouw | | 623/2.1 |
| 6,790,230 B2 | 9/2004 | Beyersdorf et al. | | 623/2.18 |
| 6,790,231 B2 | 9/2004 | Liddicoat et al. | | 623/2.37 |
| 6,793,673 B2 | 9/2004 | Kowalsky et al. | | 623/2.36 |
| 6,797,000 B2 | 9/2004 | Simpson et al. | | 623/2.15 |
| 6,797,001 B2 | 9/2004 | Mathis et al. | | 623/2.37 |
| 6,797,002 B2 | 9/2004 | Spence et al. | | 623/2.38 |
| 6,802,860 B2 | 10/2004 | Cosgrove et al. | | 623/2.11 |
| 6,805,710 B2 | 10/2004 | Bolling et al. | | 623/2.36 |
| 6,805,711 B2 | 10/2004 | Quijano et al. | | 623/2.37 |
| 6,810,882 B2 | 11/2004 | Langberg et al. | | 128/898 |
| 6,821,297 B2 | 11/2004 | Snyders | | 623/2.18 |
| 6,824,562 B2 | 11/2004 | Mathis et al. | | 623/2.36 |
| 6,830,584 B1 | 12/2004 | Seguin | | 623/2.11 |
| 6,830,585 B1 | 12/2004 | Artof et al. | | 623/2.11 |
| 6,837,902 B2 | 1/2005 | Nguyen et al. | | 623/2.13 |
| 6,840,246 B2 | 1/2005 | Downing | | 128/898 |
| 6,840,957 B2 | 1/2005 | DiMatteo et al. | | 623/1.24 |
| 6,846,324 B2 | 1/2005 | Stobie | | 623/2.11 |
| 6,846,325 B2 | 1/2005 | Liddicoat | | 623/2.4 |
| 6,858,039 B2 | 2/2005 | McCarthy | | 623/2.36 |
| 6,869,444 B2 | 3/2005 | Gabbay | | 623/2.36 |
| 6,872,226 B2 | 3/2005 | Cali et al. | | 623/2.13 |
| 6,875,224 B2 | 4/2005 | Grimes | | 606/219 |
| 6,875,230 B1 | 4/2005 | Morita et al. | | 623/2.12 |
| 6,875,231 B2 | 4/2005 | Anduiza et al. | | 623/2.14 |
| 6,881,199 B2 | 4/2005 | Wilk et al. | | 604/9 |
| 6,881,224 B2 | 4/2005 | Kruse et al. | | 623/2.11 |
| 6,883,522 B2 | 4/2005 | Spence et al. | | 128/898 |
| 6,890,352 B1 | 5/2005 | Lentell | | 623/2.27 |
| 6,890,353 B2 | 5/2005 | Cohn et al. | | 623/2.37 |
| 6,893,459 B1 | 5/2005 | Macoviak | | 623/2.11 |
| 6,893,460 B2 | 5/2005 | Spenser et al. | | 623/2.14 |
| 6,896,700 B2 | 5/2005 | Lu et al. | | 623/2.34 |
| 6,902,576 B2 | 6/2005 | Drasler et al. | | 623/1.24 |
| 6,908,478 B2 | 6/2005 | Alferness et al. | | 623/1.11 |
| 6,908,481 B2 | 6/2005 | Cribier | | 623/2.11 |
| 6,911,043 B2 | 6/2005 | Myers et al. | | 623/2.13 |
| 6,913,608 B2 | 7/2005 | Liddicoat et al. | | 606/151 |
| 6,916,338 B2 | 7/2005 | Speziali | | 623/2.12 |
| 6,918,917 B1 | 7/2005 | Nguyen et al. | | 606/139 |
| 6,921,407 B2 | 7/2005 | Nguyen et al. | | 606/142 |
| 6,921,811 B2 | 7/2005 | Zamora et al. | | 536/21 |
| 6,926,715 B1 | 8/2005 | Hauck et al. | | 606/41 |
| 6,926,730 B1 | 8/2005 | Nguyen et al. | | 606/213 |
| 6,929,653 B2 | 8/2005 | Strecter | | 606/200 |
| 6,932,838 B2 | 8/2005 | Schwartz et al. | | 623/1.23 |
| 6,936,067 B2 | 8/2005 | Buchanan | | 623/2.28 |
| 6,939,359 B2 | 9/2005 | Tu et al. | | 606/159 |
| 6,942,694 B2 | 9/2005 | Liddicoat et al. | | 623/2.36 |
| 6,945,957 B2 | 9/2005 | Freyman | | 604/96.01 |
| 6,945,978 B1 | 9/2005 | Hyde | | 606/142 |
| 6,945,996 B2 | 9/2005 | Sedransk | | 623/2.12 |
| 6,945,997 B2 | 9/2005 | Huynh et al. | | 623/2.17 |
| 6,949,122 B2 | 9/2005 | Adams et al. | | 623/2.36 |
| 6,951,571 B1 | 10/2005 | Srivastava | | 623/1.24 |
| 6,951,573 B1 | 10/2005 | Dilling | | 623/2.2 |
| 6,953,332 B1 | 10/2005 | Kurk et al. | | 425/275 |
| 6,955,689 B2 | 10/2005 | Ryan et al. | | 623/2.36 |
| 6,958,076 B2 | 10/2005 | Acosta et al. | | 623/1.24 |
| 6,962,605 B2 | 11/2005 | Cosgrove et al. | | 623/2.36 |
| 6,964,682 B2 | 11/2005 | Nguyen-Thien-Nhon et al. | | 623/2.11 |
| 6,964,683 B2 | 11/2005 | Kowalsky et al. | | 623/2.36 |
| 6,964,684 B2 | 11/2005 | Ortiz et al. | | 623/2.37 |
| 6,966,925 B2 | 11/2005 | Stobie | | 623/2.11 |
| 6,966,926 B2 | 11/2005 | Mathis | | 623/2.36 |
| 6,974,464 B2 | 12/2005 | Quijano et al. | | 606/108 |
| 6,974,474 B2 | 12/2005 | Pavcnik et al. | | 623/1.24 |
| 6,974,476 B2 | 12/2005 | McGuckin, Jr. et al. | | 623/2.36 |
| 6,976,995 B2 | 12/2005 | Mathis et al. | | 623/2.37 |
| 6,979,350 B2 | 12/2005 | Moll et al. | | 623/1.24 |
| 6,986,775 B2 | 1/2006 | Morales et al. | | 606/139 |
| 6,989,027 B2 | 1/2006 | Allen et al. | | 623/2.18 |
| 6,989,028 B2 | 1/2006 | Lashinski et al. | | 623/2.37 |
| 6,997,950 B2 | 2/2006 | Chawla | | 623/2.1 |
| 6,997,951 B2 | 2/2006 | Solem et al. | | 623/2.37 |
| 7,004,176 B2 | 2/2006 | Lau | | 128/898 |
| 7,007,396 B2 | 3/2006 | Rudko et al. | | 33/512 |
| 7,011,669 B2 | 3/2006 | Kimblad | | 606/151 |
| 7,011,681 B2 | 3/2006 | Vesely | | 623/2.11 |
| 7,011,682 B2 | 3/2006 | Lashinski et al. | | 623/2.37 |
| 7,018,406 B2 | 3/2006 | Seguin et al. | | 623/2.1 |
| 7,018,407 B1 | 3/2006 | Wright et al. | | 623/2.11 |
| 7,018,408 B2 | 3/2006 | Bailey et al. | | 623/2.11 |
| 7,022,134 B1 | 4/2006 | Quijano et al. | | 623/1.24 |
| 7,025,780 B2 | 4/2006 | Gabbay | | 623/2.13 |
| 7,033,390 B2 | 4/2006 | Johnson et al. | | 623/2.11 |
| 7,037,333 B2 | 5/2006 | Myers et al. | | 623/2.13 |
| 7,037,334 B1 | 5/2006 | Hlavka et al. | | 623/2.36 |
| 7,041,128 B2 | 5/2006 | McGuckin, Jr. et al. | | 623/1.36 |
| 7,041,132 B2 | 5/2006 | Quijano et al. | | 623/2.11 |
| 7,044,966 B2 | 5/2006 | Svanidze et al. | | 623/2.1 |
| 7,044,967 B1 | 5/2006 | Solem et al. | | 623/2.36 |
| 7,048,754 B2 | 5/2006 | Martin et al. | | 606/232 |
| 7,048,757 B2 | 5/2006 | Shaknovich | | 623/1.24 |
| 7,052,487 B2 | 5/2006 | Cohn et al. | | 604/509 |
| 7,052,507 B2 | 5/2006 | Wakuda et al. | | 606/194 |
| 7,063,722 B2 | 6/2006 | Marquez | | 623/2.36 |
| 7,066,954 B2 | 6/2006 | Ryan et al. | | 623/2.36 |
| 7,070,616 B2 | 7/2006 | Majercak et al. | | 623/1.24 |

| Patent/Pub No. | Date | Name | Class |
|---|---|---|---|
| 7,070,618 B2 | 7/2006 | Streeter | 623/2.36 |
| 7,077,862 B2 | 7/2006 | Vidlund et al. | 623/2.36 |
| 7,081,131 B2 | 7/2006 | Thornton | 623/1.24 |
| 7,087,064 B1 | 8/2006 | Hyde | 606/142 |
| 7,089,051 B2 | 8/2006 | Jäverud et al. | 600/547 |
| 7,090,695 B2 | 8/2006 | Solem et al. | 623/2.37 |
| 2001/0007956 A1* | 7/2001 | Letac et al. | 623/2.11 |
| 2001/0021872 A1* | 9/2001 | Bailey et al. | 623/1.24 |
| 2002/0138135 A1* | 9/2002 | Duerig et al. | 623/1.24 |
| 2002/0151970 A1 | 10/2002 | Garrison et al. | 623/2.11 |
| 2003/0023300 A1 | 1/2003 | Bailey et al. | 623/1.13 |
| 2003/0055492 A1 | 3/2003 | Shaolian et al. | 623/231.13 |
| 2003/0069646 A1 | 4/2003 | Stinson | 623/23.7 |
| 2003/0199971 A1 | 10/2003 | Tower et al. | 623/1.24 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.11 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | 623/1.13 |
| 2004/0019377 A1 | 1/2004 | Taylor et al. | 623/2.11 |
| 2004/0019378 A1 | 1/2004 | Hlavka et al. | 623/2.11 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.11 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/170 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0087975 A1 | 5/2004 | Lucatero et al. | 606/139 |
| 2004/0088045 A1 | 5/2004 | Cox | 623/2.13 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138742 A1 | 7/2004 | Myers et al. | 623/2.12 |
| 2004/0138743 A1 | 7/2004 | Myers et al. | 623/2.13 |
| 2004/0138744 A1 | 7/2004 | Lashinski et al. | 623/2.36 |
| 2004/0138745 A1 | 7/2004 | Macoviak et al. | 623/2.36 |
| 2004/0148018 A1 | 7/2004 | Carpentier et al. | 623/2.18 |
| 2004/0148019 A1 | 7/2004 | Vidlund et al. | 623/2.36 |
| 2004/0148020 A1 | 7/2004 | Vidlund et al. | 623/2.36 |
| 2004/0153052 A1 | 8/2004 | Mathis | 606/1 |
| 2004/0153146 A1 | 8/2004 | Lashinski et al. | 623/2.36 |
| 2004/0153147 A1 | 8/2004 | Mathis | 623/2.37 |
| 2004/0158321 A1 | 8/2004 | Reuter et al. | 623/2.36 |
| 2004/0162610 A1 | 8/2004 | Liska et al. | 623/2.11 |
| 2004/0167539 A1 | 8/2004 | Kuehn et al. | 606/108 |
| 2004/0167620 A1 | 8/2004 | Ortiz et al. | 623/2.11 |
| 2004/0172046 A1 | 9/2004 | Hlavka et al. | 606/142 |
| 2004/0176839 A1 | 9/2004 | Huynh et al. | 623/2.4 |
| 2004/0176840 A1 | 9/2004 | Langberg et al. | 623/2.37 |
| 2004/0181238 A1 | 9/2004 | Zarbatany et al. | 606/108 |
| 2004/0186444 A1 | 9/2004 | Daly et al. | 604/247 |
| 2004/0186558 A1 | 9/2004 | Pavcnik et al. | 623/1.24 |
| 2004/0186561 A1 | 9/2004 | McGuckin, Jr. et al. | 623/1.36 |
| 2004/0186563 A1 | 9/2004 | Iobbi | 623/2.11 |
| 2004/0186565 A1 | 9/2004 | Schreck | 623/2.18 |
| 2004/0186566 A1 | 9/2004 | Hindrichs et al. | 623/2.37 |
| 2004/0193147 A1 | 9/2004 | Starksen et al. | 606/153 |
| 2004/0193253 A1 | 9/2004 | Thorpe et al. | 623/1.24 |
| 2004/0193260 A1 | 9/2004 | Alferness et al. | 623/2.11 |
| 2004/0199155 A1 | 10/2004 | Mollenauer | 606/27 |
| 2004/0199183 A1 | 10/2004 | Oz et al. | 606/142 |
| 2004/0199191 A1 | 10/2004 | Schwartz | 606/159 |
| 2004/0204758 A1 | 10/2004 | Eberhardt et al. | 623/2.15 |
| 2004/0206363 A1 | 10/2004 | McCarthy et al. | 128/898 |
| 2004/0210240 A1 | 10/2004 | Saint | 606/139 |
| 2004/0210301 A1 | 10/2004 | Obermiller | 623/1.24 |
| 2004/0210303 A1 | 10/2004 | Sedransk | 623/2.1 |
| 2004/0210304 A1 | 10/2004 | Seguin et al. | 623/2.11 |
| 2004/0210305 A1 | 10/2004 | Shu et al. | 623/2.11 |
| 2004/0210306 A1 | 10/2004 | Quijano et al. | 623/2.17 |
| 2004/0210307 A1 | 10/2004 | Khairkhahan | 623/2.18 |
| 2004/0215333 A1 | 10/2004 | Duran et al. | 623/1.24 |
| 2004/0215339 A1 | 10/2004 | Drasler et al. | 623/3.1 |
| 2004/0220654 A1 | 11/2004 | Mathis et al. | 623/1.11 |
| 2004/0220657 A1 | 11/2004 | Nieminen et al. | 623/1.15 |
| 2004/0225322 A1 | 11/2004 | Garrison et al. | 606/200 |
| 2004/0225344 A1 | 11/2004 | Hoffa et al. | 623/1.1 |
| 2004/0225348 A1 | 11/2004 | Case et al. | 623/1.15 |
| 2004/0225352 A1 | 11/2004 | Osborne et al. | 623/1.24 |
| 2004/0225353 A1 | 11/2004 | McGuckin, Jr. et al. | 623/2.11 |
| 2004/0225354 A1 | 11/2004 | Allen et al. | 623/2.11 |
| 2004/0225355 A1 | 11/2004 | Stevens | 623/2.11 |
| 2004/0225356 A1 | 11/2004 | Frater | 623/2.14 |
| 2004/0230117 A1 | 11/2004 | Tosaya et al. | 600/439 |
| 2004/0230297 A1 | 11/2004 | Thornton | 623/1.24 |
| 2004/0236411 A1 | 11/2004 | Sarac et al. | 623/1.26 |
| 2004/0236418 A1 | 11/2004 | Stevens | 623/2.11 |
| 2004/0236419 A1 | 11/2004 | Milo | 623/2.36 |
| 2004/0243153 A1 | 12/2004 | Liddicoat et al. | 606/151 |
| 2004/0243219 A1 | 12/2004 | Fischer et al. | 623/1.15 |
| 2004/0243227 A1 | 12/2004 | Starksen et al. | 623/2.11 |
| 2004/0243228 A1 | 12/2004 | Kowalsky et al. | 623/2.11 |
| 2004/0243230 A1 | 12/2004 | Navia et al. | 623/2.36 |
| 2004/0249452 A1 | 12/2004 | Adams et al. | 623/2.36 |
| 2004/0254600 A1 | 12/2004 | Zarbatany et al. | 606/194 |
| 2004/0254636 A1 | 12/2004 | Flagle et al. | 623/1.24 |
| 2004/0260276 A1 | 12/2004 | Rudko et al. | 606/15 |
| 2004/0260317 A1 | 12/2004 | Bloom et al. | 606/151 |
| 2004/0260322 A1 | 12/2004 | Rudko et al. | 606/167 |
| 2004/0260389 A1 | 12/2004 | Case et al. | 623/1.24 |
| 2004/0260390 A1 | 12/2004 | Sarac et al. | 623/1.24 |
| 2004/0260393 A1 | 12/2004 | Rahdert et al. | 623/2.36 |

| | | | | | | | |
|---|---|---|---|---|---|---|---|
| 2004/0260394 A1 | 12/2004 | Douk et al. | 623/2.36 | 2005/0137682 A1 | 6/2005 | Justino | 623/1.24 |
| 2004/0267357 A1 | 12/2004 | Allen et al. | 623/2.11 | 2005/0137685 A1 | 6/2005 | Nieminen et al. | 623/2.11 |
| 2005/0004583 A1 | 1/2005 | Oz et al. | 606/142 | 2005/0137686 A1 | 6/2005 | Salahieh et al. | 623/2.11 |
| 2005/0004667 A1 | 1/2005 | Swinford et al. | 623/2.36 | 2005/0137688 A1 | 6/2005 | Salahieh et al. | 623/2.11 |
| 2005/0010285 A1 | 1/2005 | Lambrecht et al. | 623/2.18 | 2005/0137689 A1 | 6/2005 | Salahieh et al. | 623/2.11 |
| 2005/0010287 A1 | 1/2005 | Macoviak et al. | 623/2.36 | 2005/0137690 A1 | 6/2005 | Salahieh et al. | 623/2.11 |
| 2005/0015112 A1 | 1/2005 | Cohn et al. | 606/200 | 2005/0137691 A1 | 6/2005 | Salahieh et al. | 623/2.11 |
| 2005/0021056 A1 | 1/2005 | St. Goar et al. | 606/144 | 2005/0137692 A1 | 6/2005 | Haug et al. | 623/2.11 |
| 2005/0021136 A1 | 1/2005 | Xie et al. | 623/2.14 | 2005/0137693 A1 | 6/2005 | Haug et al. | 623/2.11 |
| 2005/0027261 A1 | 2/2005 | Weaver et al. | 604/246 | 2005/0137694 A1 | 6/2005 | Haug et al. | 623/2.11 |
| 2005/0027348 A1 | 2/2005 | Case et al. | 623/1.24 | 2005/0137696 A1 | 6/2005 | Salahieh et al. | 623/2.11 |
| 2005/0027351 A1 | 2/2005 | Reuter et al. | 623/2.11 | 2005/0137697 A1 | 6/2005 | Salahieh et al. | 623/2.11 |
| 2005/0027353 A1 | 2/2005 | Alferness et al. | 623/2.11 | 2005/0137698 A1 | 6/2005 | Salahieh et al. | 623/2.11 |
| 2005/0033398 A1 | 2/2005 | Seguin | 623/1.11 | 2005/0137699 A1 | 6/2005 | Salahieh et al. | 623/2.11 |
| 2005/0033419 A1 | 2/2005 | Alferness et al. | 623/2.11 | 2005/0137700 A1 | 6/2005 | Spence et al. | 623/2.36 |
| 2005/0033446 A1 | 2/2005 | Deem et al. | 623/23.6 | 2005/0137701 A1 | 6/2005 | Salahieh et al. | 623/2.38 |
| 2005/0038506 A1 | 2/2005 | Webler et al. | 623/2.11 | 2005/0137702 A1 | 6/2005 | Haug et al. | 623/2.38 |
| 2005/0038507 A1 | 2/2005 | Alferness et al. | 623/2.11 | 2005/0143807 A1 | 6/2005 | Pavcnik et al. | 623/1.24 |
| 2005/0043790 A1 | 2/2005 | Seguin | 623/2.18 | 2005/0143809 A1 | 6/2005 | Salahieh et al. | 623/2.11 |
| 2005/0043792 A1 | 2/2005 | Solem et al. | 623/2.36 | 2005/0143810 A1 | 6/2005 | Dauner et al. | 623/2.12 |
| 2005/0049679 A1 | 3/2005 | Taylor et al. | 623/1.15 | 2005/0143811 A1 | 6/2005 | Realyvasquez | 623/2.36 |
| 2005/0049692 A1 | 3/2005 | Numamoto et al. | 623/1.24 | 2005/0149014 A1 | 7/2005 | Hauck et al. | 606/41 |
| 2005/0049696 A1 | 3/2005 | Siess et al. | 623/2.11 | 2005/0149179 A1 | 7/2005 | Mathis et al. | 623/2.11 |
| 2005/0049697 A1 | 3/2005 | Sievers | 623/2.26 | 2005/0149180 A1 | 7/2005 | Mathis et al. | 623/2.14 |
| 2005/0054977 A1 | 3/2005 | Laird et al. | 604/96.01 | 2005/0149181 A1 | 7/2005 | Eberhardt | 623/2.14 |
| 2005/0055079 A1 | 3/2005 | Duran | 623/1.13 | 2005/0159810 A1 | 7/2005 | Filsoufi | 623/2.1 |
| 2005/0055087 A1 | 3/2005 | Starksen | 623/2.11 | 2005/0159811 A1 | 7/2005 | Lane | 623/2.14 |
| 2005/0055088 A1 | 3/2005 | Liddicoat et al. | 623/2.11 | 2005/0165477 A1 | 7/2005 | Anduiza et al. | 623/2.11 |
| 2005/0055089 A1 | 3/2005 | Macoviak et al. | 623/2.37 | 2005/0165478 A1 | 7/2005 | Song | 623/2.22 |
| 2005/0060029 A1 | 3/2005 | Le et al. | 623/2.11 | 2005/0171472 A1 | 8/2005 | Lutter | 604/101.03 |
| 2005/0060030 A1 | 3/2005 | Lashinski et al. | 623/2.37 | 2005/0171601 A1 | 8/2005 | Cosgrove et al. | 623/2.11 |
| 2005/0065460 A1 | 3/2005 | Laird | 604/20 | 2005/0177227 A1 | 8/2005 | Heim et al. | 623/2.12 |
| 2005/0065550 A1 | 3/2005 | Starksen et al. | 606/219 | 2005/0177228 A1 | 8/2005 | Solem et al. | 623/2.36 |
| 2005/0065594 A1 | 3/2005 | Dimatteo et al. | 623/1.24 | 2005/0182483 A1 | 8/2005 | Osborne et al. | 623/1.24 |
| 2005/0065597 A1 | 3/2005 | Lansac | 623/2.11 | 2005/0184122 A1 | 8/2005 | Hlavka et al. | 227/175.1 |
| 2005/0070998 A1 | 3/2005 | Rourke et al. | 623/2.11 | 2005/0187614 A1 | 8/2005 | Agnew | 623/1.24 |
| 2005/0075584 A1 | 4/2005 | Cali | 600/587 | 2005/0187616 A1 | 8/2005 | Realyvasquez | 623/2.11 |
| 2005/0075659 A1 | 4/2005 | Realyvasquez et al. | 606/167 | 2005/0187617 A1 | 8/2005 | Navia | 623/2.13 |
| 2005/0075662 A1 | 4/2005 | Pedersen et al. | 606/194 | 2005/0192606 A1 | 9/2005 | Paul, Jr. et al. | 606/159 |
| 2005/0075712 A1 | 4/2005 | Biancucci et al. | 623/1.11 | 2005/0192665 A1 | 9/2005 | Spenser et al. | 623/2.11 |
| 2005/0075713 A1 | 4/2005 | Biancucci et al. | 623/1.11 | 2005/0197692 A1 | 9/2005 | Pai et al. | 623/2.1 |
| 2005/0075717 A1 | 4/2005 | Nguyen et al. | 623/1.26 | 2005/0197693 A1 | 9/2005 | Pai et al. | 623/2.1 |
| 2005/0075718 A1 | 4/2005 | Nguyen et al. | 623/1.26 | 2005/0197694 A1 | 9/2005 | Pai et al. | 623/2.1 |
| 2005/0075719 A1 | 4/2005 | Bergheim | 623/1.26 | 2005/0203549 A1 | 9/2005 | Realyvasquez | 606/142 |
| 2005/0075720 A1 | 4/2005 | Nguyen et al. | 623/1.26 | 2005/0203605 A1 | 9/2005 | Dolan | 623/1.11 |
| 2005/0075723 A1 | 4/2005 | Schroeder et al. | 623/2.1 | 2005/0203614 A1 | 9/2005 | Forster et al. | 623/2.11 |
| 2005/0075724 A1 | 4/2005 | Svanidze et al. | 623/2.11 | 2005/0203615 A1 | 9/2005 | Forster et al. | 623/2.11 |
| 2005/0075725 A1 | 4/2005 | Rowe | 623/2.14 | 2005/0203616 A1 | 9/2005 | Cribier | 623/2.11 |
| 2005/0075726 A1 | 4/2005 | Svanidze et al. | 623/2.14 | 2005/0203617 A1 | 9/2005 | Forster et al. | 623/2.14 |
| 2005/0075728 A1 | 4/2005 | Nguyen et al. | 623/2.17 | 2005/0203618 A1 | 9/2005 | Sharkawy et al. | 623/2.38 |
| 2005/0075729 A1 | 4/2005 | Nguyen et al. | 623/2.18 | 2005/0216039 A1 | 9/2005 | Lederman | 606/144 |
| 2005/0075730 A1 | 4/2005 | Myers et al. | 623/2.18 | 2005/0216077 A1 | 9/2005 | Mathis et al. | 623/2.11 |
| 2005/0075731 A1 | 4/2005 | Artof et al. | 623/2.18 | 2005/0216078 A1 | 9/2005 | Starksen et al. | 623/2.11 |
| 2005/0080483 A1 | 4/2005 | Solem et al. | 623/2.11 | 2005/0222675 A1 | 10/2005 | Sauter | 623/1.26 |
| 2005/0085900 A1 | 4/2005 | Case et al. | 623/1.24 | 2005/0222678 A1 | 10/2005 | Lashinski et al. | 623/2.11 |
| 2005/0085903 A1 | 4/2005 | Lau | 623/2.11 | 2005/0228422 A1 | 10/2005 | Machold et al. | 606/167 |
| 2005/0085904 A1 | 4/2005 | Lemmon | 623/2.11 | 2005/0228479 A1 | 10/2005 | Pavcnik et al. | 623/1.11 |
| 2005/0090846 A1 | 4/2005 | Pedersen et al. | 606/159 | 2005/0228486 A1 | 10/2005 | Case et al. | 623/1.24 |
| 2005/0096735 A1 | 5/2005 | Hojeibane et al. | 623/1.24 | 2005/0228494 A1 | 10/2005 | Marquez | 623/2.18 |
| 2005/0096738 A1 | 5/2005 | Cali et al. | 623/2.18 | 2005/0228495 A1 | 10/2005 | Macoviak | 623/2.18 |
| 2005/0096739 A1 | 5/2005 | Cao | 623/2.19 | 2005/0228496 A1 | 10/2005 | Mensah et al. | 623/2.41 |
| 2005/0096740 A1 | 5/2005 | Langberg et al. | 623/2.36 | 2005/0234541 A1 | 10/2005 | Hunt et al. | 623/1.24 |
| 2005/0101975 A1 | 5/2005 | Nguyen et al. | 606/151 | 2005/0234546 A1 | 10/2005 | Nugent et al. | 623/1.36 |
| 2005/0102026 A1 | 5/2005 | Turner et al. | 623/2.1 | 2005/0240200 A1 | 10/2005 | Bergheim | 606/108 |
| 2005/0107810 A1 | 5/2005 | Morales et al. | 606/143 | 2005/0240202 A1 | 10/2005 | Shennib et al. | 606/142 |
| 2005/0107811 A1 | 5/2005 | Starksen et al. | 606/143 | 2005/0240255 A1 | 10/2005 | Schaeffer | 623/1.11 |
| 2005/0107812 A1 | 5/2005 | Starksen et al. | 606/143 | 2005/0240259 A1 | 10/2005 | Sisken et al. | 623/1.36 |
| 2005/0107872 A1 | 5/2005 | Mensah et al. | 623/2.14 | 2005/0240262 A1 | 10/2005 | White | 623/2.12 |
| 2005/0113910 A1 | 5/2005 | Paniagua et al. | 623/2.14 | 2005/0244460 A1 | 11/2005 | Alferiev et al. | 424/426 |
| 2005/0119673 A1 | 6/2005 | Gordon et al. | 606/151 | 2005/0246013 A1 | 11/2005 | Gabbay | 623/2.1 |
| 2005/0119734 A1 | 6/2005 | Spence et al. | 623/2.11 | 2005/0251251 A1 | 11/2005 | Cribier | 623/2.1 |
| 2005/0119735 A1 | 6/2005 | Spence et al. | 623/2.36 | 2005/0256566 A1 | 11/2005 | Gabbay | 623/2.1 |
| 2005/0125011 A1 | 6/2005 | Spence et al. | 606/144 | 2005/0261704 A1 | 11/2005 | Mathis | 606/108 |
| 2005/0131438 A1 | 6/2005 | Cohn | 606/170 | 2005/0261759 A1 | 11/2005 | Lambrecht et al. | 623/1.26 |
| 2005/0137449 A1 | 6/2005 | Nieminen et al. | 600/37 | 2005/0267493 A1 | 12/2005 | Schreck et al. | 606/139 |
| 2005/0137450 A1 | 6/2005 | Aronson et al. | 600/37 | 2005/0267560 A1 | 12/2005 | Bates | 623/1.1 |
| 2005/0137451 A1 | 6/2005 | Gordon et al. | 600/37 | 2005/0267565 A1 | 12/2005 | Dave et al. | 623/1.15 |
| 2005/0137676 A1 | 6/2005 | Richardson et al. | 623/1.11 | 2005/0267571 A1 | 12/2005 | Spence et al. | 623/2.11 |
| 2005/0137681 A1 | 6/2005 | Shoemaker et al. | 623/1.23 | 2005/0267573 A9 | 12/2005 | Macoviak et al. | 623/2.36 |

| Publication No. | Date | Inventor | Class |
|---|---|---|---|
| 2005/0267574 A1 | 12/2005 | Cohn et al. | 623/2.36 |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009804 A1 | 1/2006 | Pederson | 607/2 |
| 2006/0009841 A1 | 1/2006 | McGuckin, Jr. et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | 623/2.37 |
| 2006/0025750 A1 | 2/2006 | Starksen et al. | 604/510 |
| 2006/0025784 A1 | 2/2006 | Starksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | 606/219 |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/194 |
| 2006/0047338 A1 | 3/2006 | Jenson | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | 623/2.18 |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069429 A1 | 3/2006 | Spence et al. | 623/2.11 |
| 2006/0069430 A9 | 3/2006 | Rahdert et al. | 623/2.36 |
| 2006/0074483 A1 | 4/2006 | Schrayer | 623/2.1 |
| 2006/0074484 A1 | 4/2006 | Huber | 623/2.11 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.11 |
| 2006/0100699 A1 | 5/2006 | Vidlund et al. | 623/2.36 |
| 2006/0106278 A1 | 5/2006 | Machold et al. | 600/37 |
| 2006/0106279 A1 | 5/2006 | Machold et al. | 600/37 |
| 2006/0106456 A9 | 5/2006 | Machold et al. | 623/2.36 |
| 2006/0111660 A1 | 5/2006 | Wolf et al. | 604/9 |
| 2006/0111773 A1 | 5/2006 | Rittgers et al. | 623/1.24 |
| 2006/0111774 A1 | 5/2006 | Samkov et al. | 623/2.25 |
| 2006/0116572 A1 | 6/2006 | Case | 600/424 |
| 2006/0116756 A1 | 6/2006 | Solem et al. | 623/2.11 |
| 2006/0122686 A1 | 6/2006 | Gilad et al. | 623/1.13 |
| 2006/0122692 A1 | 6/2006 | Gilad et al. | 623/1.24 |
| 2006/0122693 A1 | 6/2006 | Biadillah et al. | 623/1.24 |
| 2006/0127443 A1 | 6/2006 | Helmus | 424/423 |
| 2006/0129235 A1 | 6/2006 | Seguin et al. | 623/2.11 |
| 2006/0129236 A1 | 6/2006 | McCarthy | 623/2.36 |
| 2006/0135476 A1 | 6/2006 | Kutryk et al. | 514/59 |
| 2006/0135964 A1 | 6/2006 | Vesely | 606/108 |
| 2006/0135967 A1 | 6/2006 | Realyvasquez | 606/142 |
| 2006/0136044 A1 | 6/2006 | Osborne et al. | 623/1.24 |
| 2006/0136045 A1 | 6/2006 | Flagle et al. | 623/1.24 |
| 2006/0136052 A1 | 6/2006 | Vesely | 623/2.18 |
| 2006/0136054 A1 | 6/2006 | Berg et al. | 623/2.38 |
| 2006/0142846 A1 | 6/2006 | Pavcnik et al. | 623/1.24 |
| 2006/0142847 A1 | 6/2006 | Shaknovich | 623/1.24 |
| 2006/0142848 A1 | 6/2006 | Gabbay | 623/1.26 |
| 2006/0142854 A1 | 6/2006 | Alferness et al. | 623/2.11 |
| 2006/0149358 A1 | 7/2006 | Zilla et al. | 623/1.22 |
| 2006/0149360 A1 | 7/2006 | Schwammenthal et al. | 623/1.24 |
| 2006/0149367 A1 | 7/2006 | Sieracki | 623/2.21 |
| 2006/0149368 A1 | 7/2006 | Spence | 623/2.37 |
| 2006/0161133 A1 | 7/2006 | Laird et al. | 604/509 |
| 2006/0161248 A1 | 7/2006 | Case et al. | 623/2.1 |
| 2006/0161249 A1 | 7/2006 | Realyvasquez et al. | 623/2.11 |
| 2006/0161250 A1 | 7/2006 | Shaw | 623/2.17 |
| 2006/0167468 A1 | 7/2006 | Gabbay | 606/108 |
| 2006/0167541 A1 | 7/2006 | Lattouf | 623/2.11 |
| 2006/0167542 A1 | 7/2006 | Quintessenza | 623/2.12 |
| 2006/0167543 A1 | 7/2006 | Bailey et al. | 623/2.18 |

FOREIGN PATENT DOCUMENTS

| | | |
|---|---|---|
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |
| WO | WO 2004/045378 | 6/2004 |
| WO | WO 2004/045463 | 6/2004 |
| WO | WO 2004/047677 | 6/2004 |
| WO | WO 2004/060217 | 7/2004 |
| WO | WO 2004/060470 | 7/2004 |
| WO | WO 2004/062725 | 7/2004 |
| WO | WO 2004/066803 | 8/2004 |
| WO | WO 2004/066826 | 8/2004 |
| WO | WO 2004/069287 | 8/2004 |
| WO | WO2004/075789 | 9/2004 |
| WO | WO2004/080352 | 9/2004 |
| WO | WO2004/082523 | 9/2004 |
| WO | WO2004/082527 | 9/2004 |
| WO | WO2004/082528 | 9/2004 |
| WO | WO2004/082536 | 9/2004 |
| WO | WO2004/082537 | 9/2004 |
| WO | WO2004/082538 | 9/2004 |
| WO | WO2004/082757 | 9/2004 |
| WO | WO 2004/084746 | 10/2004 |
| WO | WO 2004/084770 | 10/2004 |
| WO | WO 2004/089246 | 10/2004 |
| WO | WO 2004/089250 | 10/2004 |
| WO | WO 2004/089253 | 10/2004 |
| WO | WO 2004/091449 | 10/2004 |
| WO | WO 2004/091454 | 10/2004 |
| WO | WO 2004/093638 | 11/2004 |
| WO | WO 2004/093726 | 11/2004 |
| WO | WO 2004/093728 | 11/2004 |
| WO | WO 2004/093730 | 11/2004 |
| WO | WO 2004/093745 | 11/2004 |
| WO | WO 2004/093935 | 11/2004 |
| WO | WO 2004/096100 | 11/2004 |
| WO | WO 2004/103222 | 12/2004 |
| WO | WO 2004/105584 | 12/2004 |
| WO | WO 2004/105651 | 12/2004 |
| WO | WO 2004/112582 | 12/2004 |
| WO | WO 2004/112585 | 12/2004 |
| WO | WO 2004/112643 | 12/2004 |
| WO | WO 2004/112652 | 12/2004 |
| WO | WO 2004/112657 | 12/2004 |
| WO | WO 2004/112658 | 12/2004 |

| | | | | | | |
|---|---|---|---|---|---|---|
| WO | WO 2004/203223 | 12/2004 | | WO | WO 2006/000763 | 1/2006 |
| WO | WO 2005/000152 | 1/2005 | | WO | WO 2006/000776 | 1/2006 |
| WO | WO 2005/002424 | 1/2005 | | WO | WO 2006/002492 | 1/2006 |
| WO | WO 2005/002466 | 1/2005 | | WO | WO 2006/004679 | 1/2006 |
| WO | WO 2005/004753 | 1/2005 | | WO | WO 2006/005015 | 1/2006 |
| WO | WO 2005/007017 | 1/2005 | | WO | WO 2006/009690 | 1/2006 |
| WO | WO 2005/007018 | 1/2005 | | WO | WO 2006/011127 | 2/2006 |
| WO | WO 2005/007036 | 1/2005 | | WO | WO 2006/012011 | 2/2006 |
| WO | WO 2005/007037 | 1/2005 | | WO | WO 2006/012013 | 2/2006 |
| WO | WO 2005/009285 | 2/2005 | | WO | WO 2006/012038 | 2/2006 |
| WO | WO 2005/009286 | 2/2005 | | WO | WO 2006/012068 | 2/2006 |
| WO | WO 2005/009505 | 2/2005 | | WO | WO 2006/012322 | 2/2006 |
| WO | WO 2005/009506 | 2/2005 | | WO | WO 2006/019498 | 2/2006 |
| WO | WO 2005/011473 | 2/2005 | | WO | WO 2006/026371 | 3/2006 |
| WO | WO 2005/011534 | 2/2005 | | WO | WO 2006/026377 | 3/2006 |
| WO | WO 2005/011535 | 2/2005 | | WO | WO 2006/026912 | 3/2006 |
| WO | WO 2005/013860 | 2/2005 | | WO | WO 2006/027499 | 3/2006 |
| WO | WO 2005/018507 | 3/2005 | | WO | WO 2006/028821 | 3/2006 |
| WO | WO 2005/021063 | 3/2005 | | WO | WO 2006/029062 | 3/2006 |
| WO | WO 2005/023155 | 3/2005 | | WO | WO 2006/031436 | 3/2006 |
| WO | WO 2005/025644 | 3/2005 | | WO | WO 2006/031469 | 3/2006 |
| WO | WO 2005/027790 | 3/2005 | | WO | WO 2006/032051 | 3/2006 |
| WO | WO 2005/027797 | 3/2005 | | WO | WO 2006/034245 | 3/2006 |
| WO | WO 2005/034812 | 4/2005 | | WO | WO 2006/035415 | 4/2006 |
| WO | WO 2005/039428 | 5/2005 | | WO | WO 2006/041505 | 4/2006 |
| WO | WO 2005/039452 | 5/2005 | | WO | WO 2006/044679 | 4/2006 |
| WO | WO 2005/046488 | 5/2005 | | WO | WO 2006/048664 | 5/2006 |
| WO | WO 2005/046528 | 5/2005 | | WO | WO 2006/050459 | 5/2006 |
| WO | WO 2005/046529 | 5/2005 | | WO | WO 2006/050460 | 5/2006 |
| WO | WO 2005/046530 | 5/2005 | | WO | WO 2006/054107 | 5/2006 |
| WO | WO 2005/046531 | 5/2005 | | WO | WO 2006/054930 | 5/2006 |
| WO | WO 2005/048883 | 6/2005 | | WO | WO 2006/055982 | 5/2006 |
| WO | WO 2005/049103 | 6/2005 | | WO | WO 2006/060546 | 6/2006 |
| WO | WO 2005/051226 | 6/2005 | | WO | WO 2006/063108 | 6/2006 |
| WO | WO 2005/055811 | 6/2005 | | WO | WO 2006/063181 | 6/2006 |
| WO | WO 2005/055883 | 6/2005 | | WO | WO 2006/063199 | 6/2006 |
| WO | WO 2005/058206 | 6/2005 | | WO | WO 2006/064490 | 6/2006 |
| WO | WO 2005/065585 | 7/2005 | | WO | WO 2006/065212 | 6/2006 |
| WO | WO 2005/065593 | 7/2005 | | WO | WO 2006/065930 | 6/2006 |
| WO | WO 2005/065594 | 7/2005 | | WO | WO 2006/066148 | 6/2006 |
| WO | WO 2005/070342 | 8/2005 | | WO | WO 2006/066150 | 6/2006 |
| WO | WO 2005/070343 | 8/2005 | | WO | WO 2006/069094 | 6/2006 |
| WO | WO 2005/072654 | 8/2005 | | WO | WO 2006/070372 | 7/2006 |
| WO | WO 2005/072655 | 8/2005 | | WO | WO 2006/073628 | 7/2006 |
| WO | WO 2005/079706 | 9/2005 | | WO | WO 2006/076890 | 7/2006 |
| WO | WO 2005/082288 | 9/2005 | | | | |
| WO | WO 2005/082289 | 9/2005 | | | | |
| WO | WO 2005/084595 | 9/2005 | | | | |
| WO | WO 2005/087139 | 9/2005 | | | | |
| WO | WO 2005/087140 | 9/2005 | | | | |

OTHER PUBLICATIONS

US 6,723,117, 04/2004, Menz et al. (withdrawn)

* cited by examiner

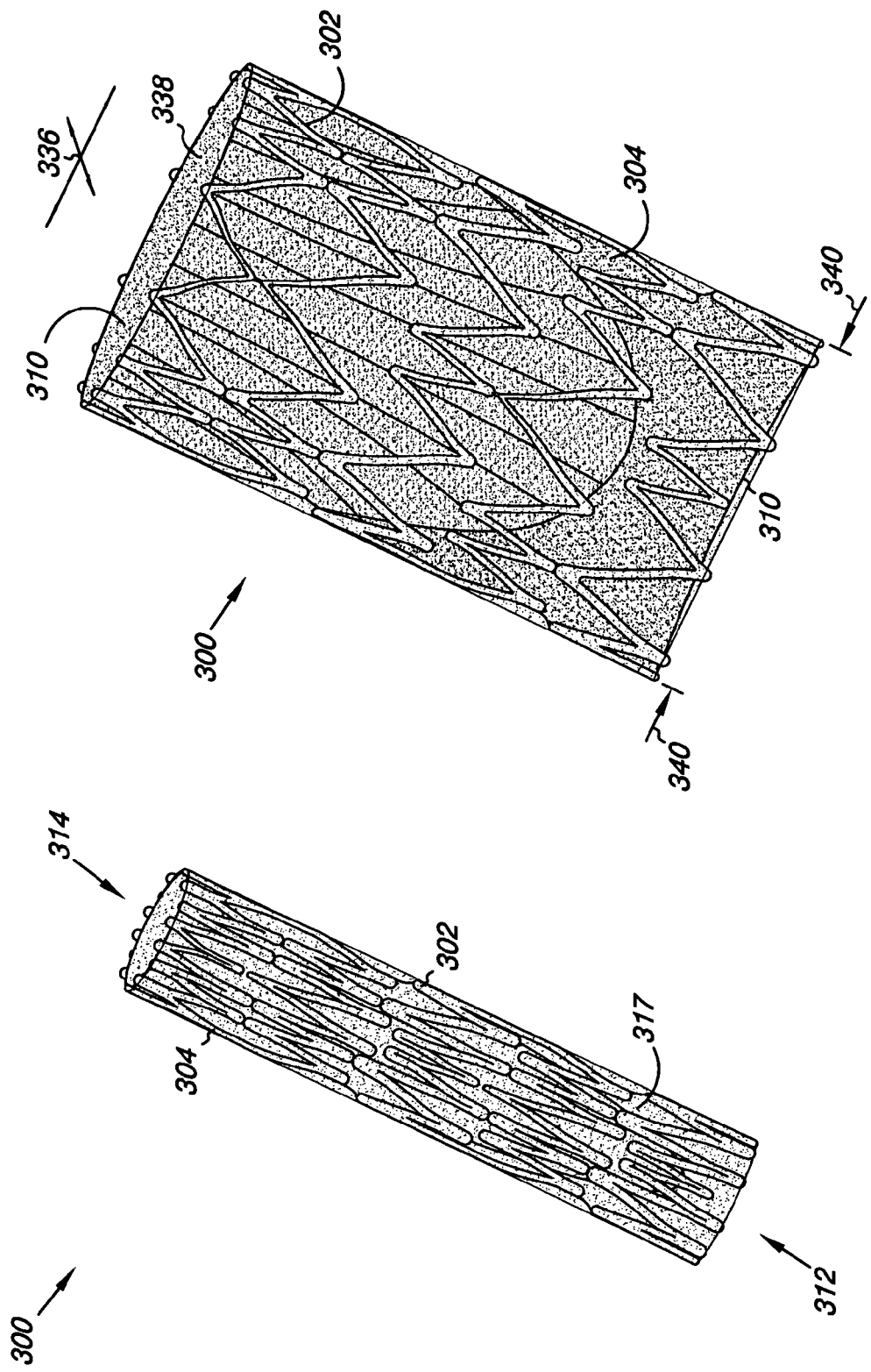

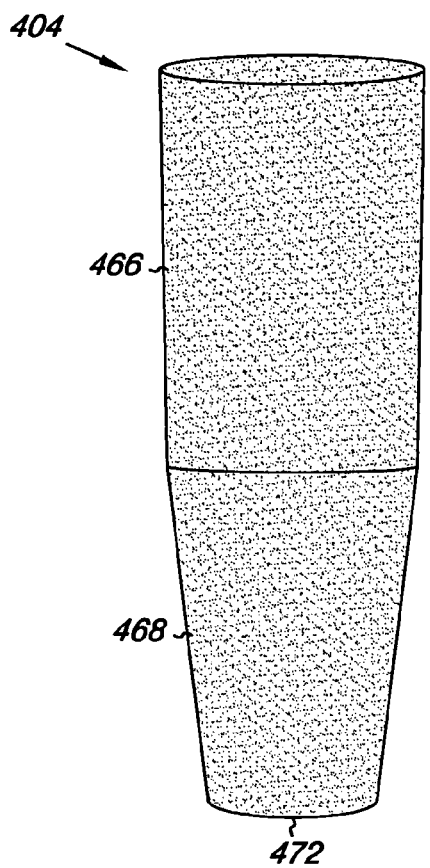
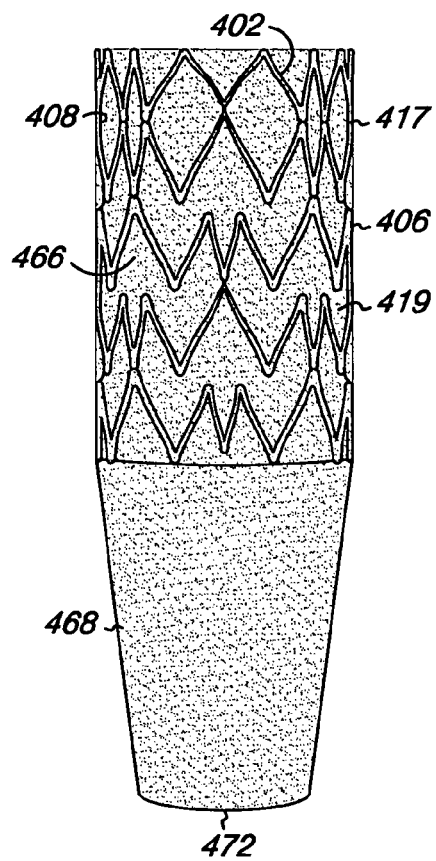
Fig. 4A
Fig. 4B
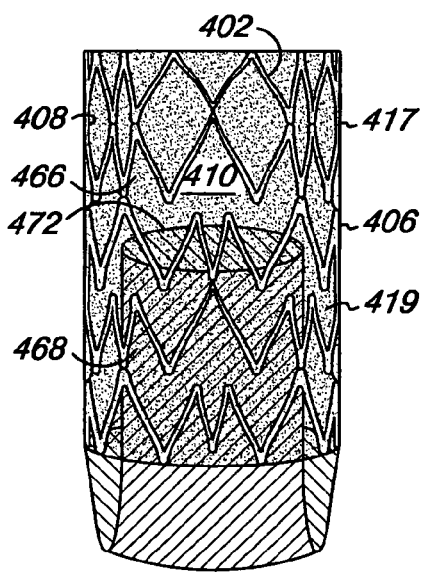
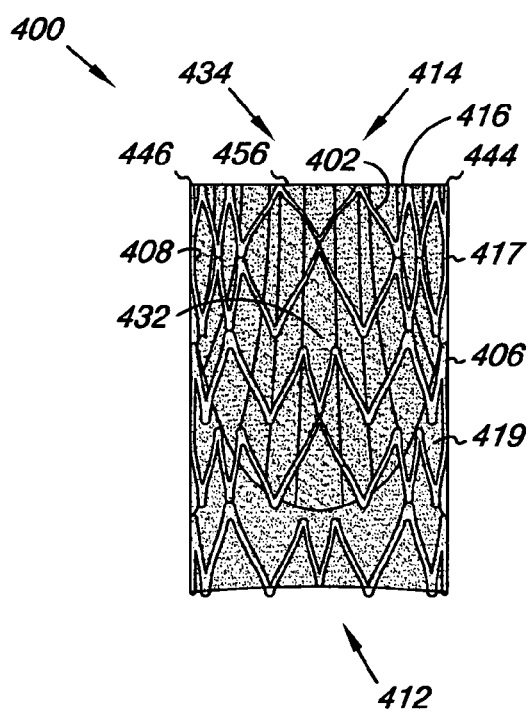
Fig. 4C
Fig. 4D

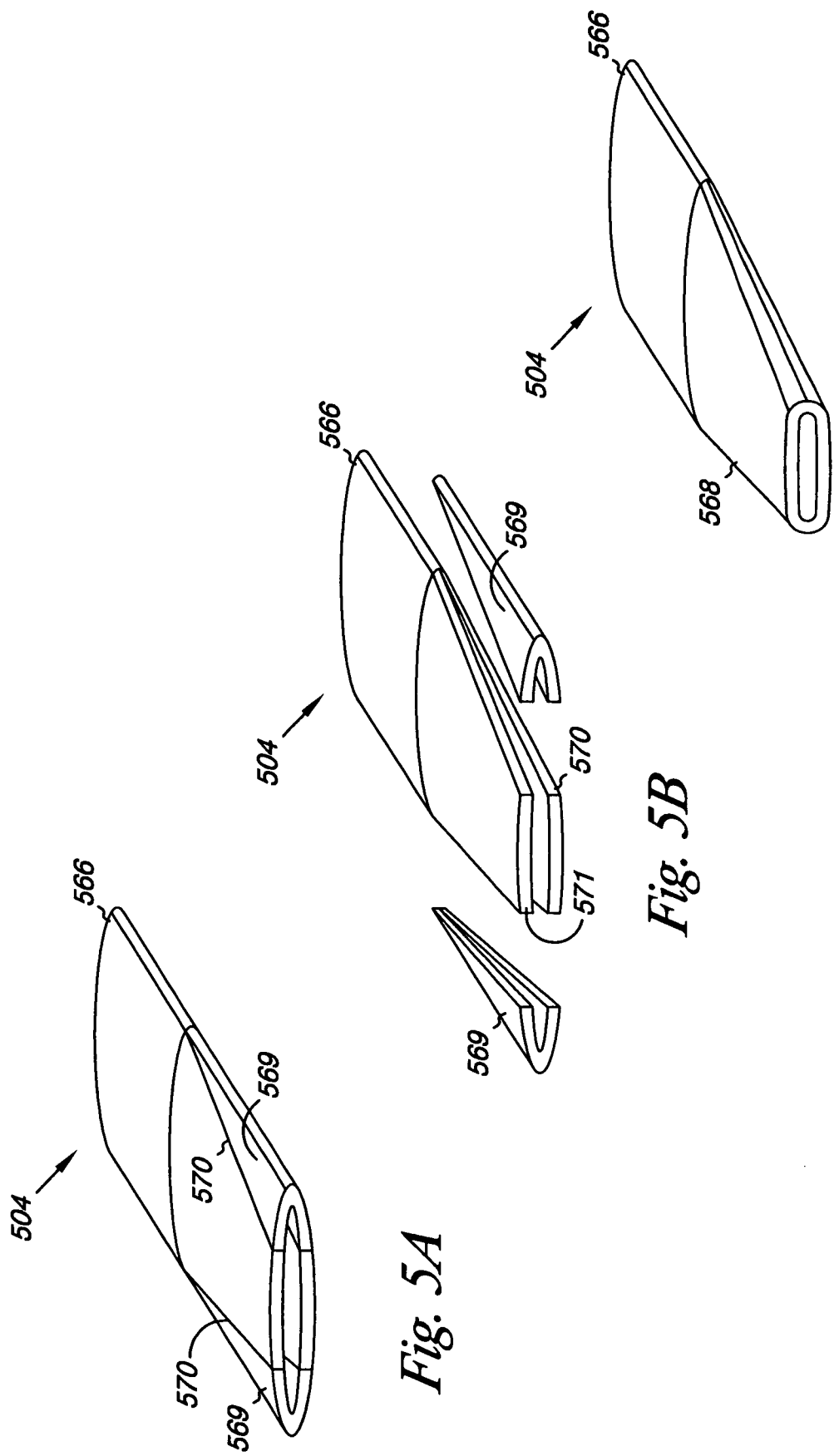

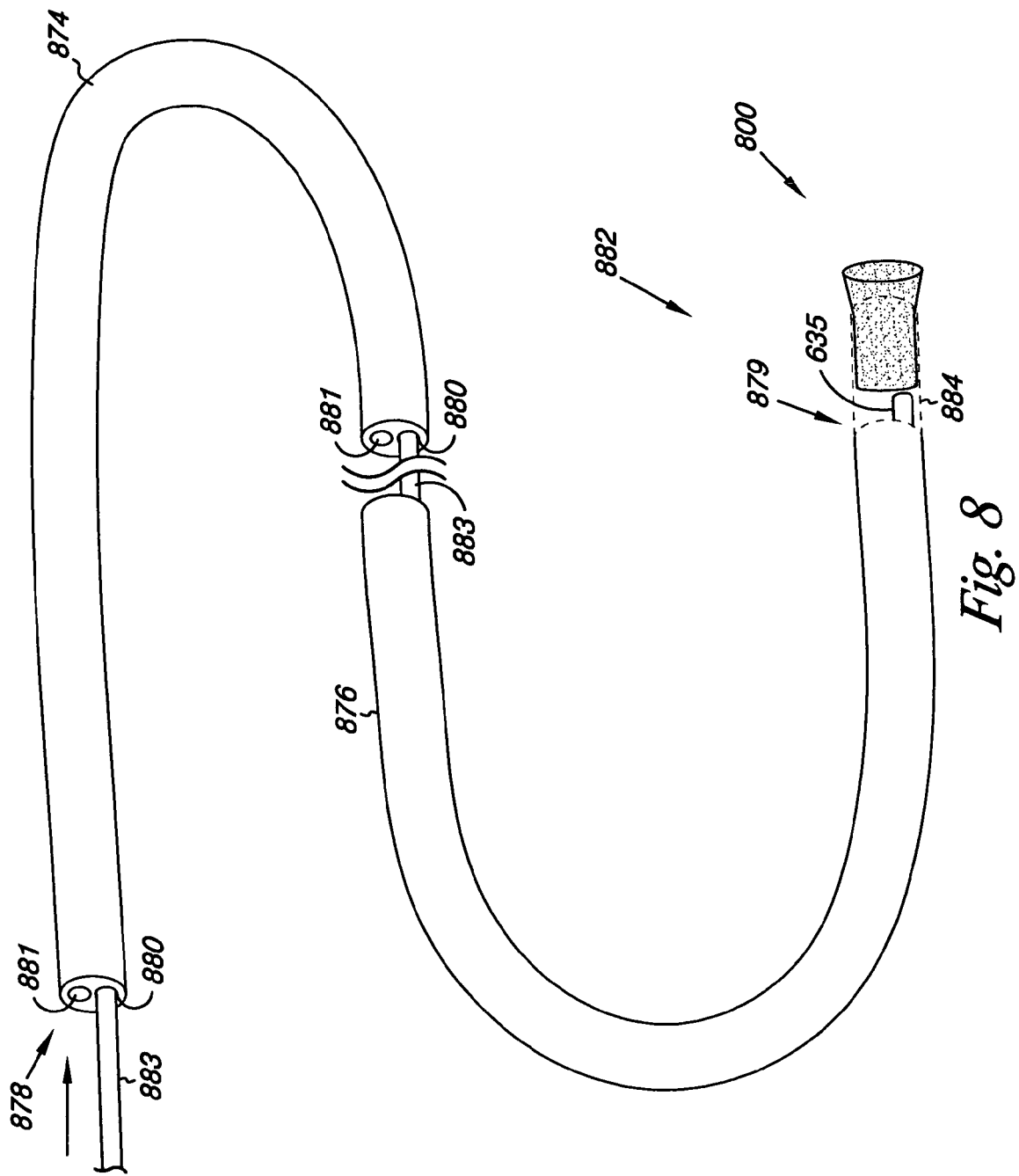

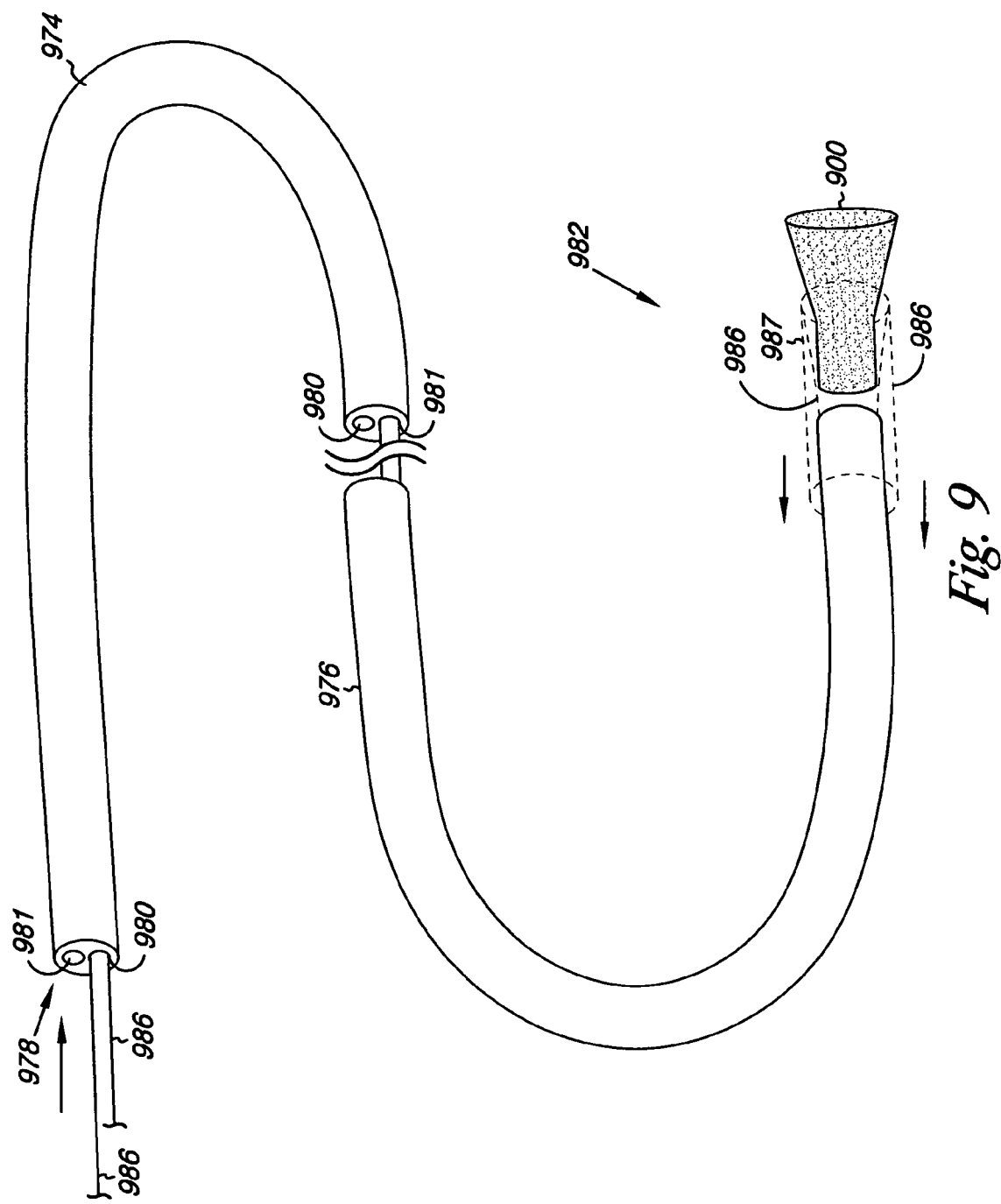

VENOUS VALVE APPARATUS, SYSTEM, AND METHOD

FIELD OF THE INVENTION

The present invention relates generally to apparatus, systems, and methods for use in a lumen; and more particularly to venous valve apparatus, systems, and methods for use in the vasculature system.

BACKGROUND OF THE INVENTION

The venous system of the legs uses pumps and valves to return blood to the heart. Venous valves create one way flow to prevent blood from flowing away from the heart. When valves fail, blood can pool in the lower legs resulting in swelling and ulcers of the leg. The absence of functioning venous valves can lead to chronic venous insufficiency.

Techniques for both repairing and replacing the valves exist, but are tedious and require invasive surgical procedures. Direct and indirect valvuoplasty procedures are used to repair damaged valves. Transposition and transplantation are used to replace an incompetent valve. Transposition involves moving a vein with an incompetent valve to a site with a competent valve. Transplantation replaces an incompetent valve with a harvested valve from another venous site. Prosthetic valves can be transplanted into the venous system, but current devices are not successful enough to see widespread usage.

BRIEF DESCRIPTION OF THE DRAWINGS

FIGS. 3A and 3B illustrate an embodiment of a valve in a compressed state (FIG. 3A) and in an expanded state (FIG. 3B).

FIGS. 4A-4D illustrate an embodiment of forming a valve.
FIGS. 5A-5C illustrate an embodiment of forming a cover.
FIGS. 6A-4E illustrate an embodiment of forming a valve.
FIG. 8 illustrates an embodiment of a system that includes a valve.
FIG. 9 illustrates an embodiment of a system that includes a valve.

DETAILED DESCRIPTION

Figure 1A:
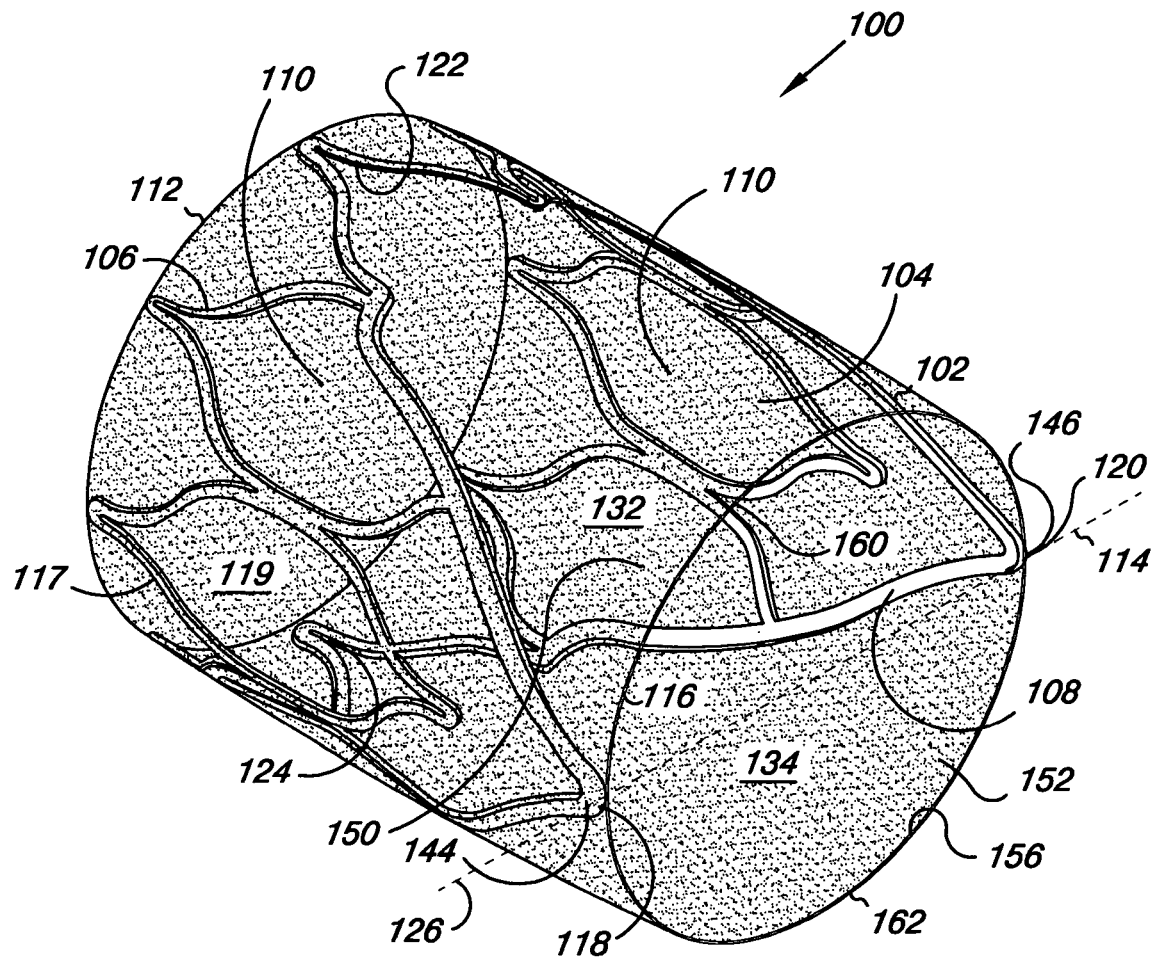
FIGS. 1A and 1B illustrate an embodiment of a valve.

Embodiments of the present invention are directed to an apparatus, system, and method for valve replacement. For example, the apparatus can include a valve that can be used to replace an incompetent valve in a body lumen. Embodiments of the valve can include a tubular frame and cover that can be implanted through minimally-invasive techniques into the body lumen. In one example, embodiments of the apparatus, system, and method for valve replacement may help to maintain antegrade blood flow, while decreasing retrograde blood flow in a venous system of individuals having venous insufficiency, such as venous insufficiency in the legs.

The Figures herein follow a numbering convention in which the first digit or digits correspond to the drawing Figure number and the remaining digits identify an element or component in the drawing. Similar elements or components between different Figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of valve.

FIGS. 1A-3 provide illustrations of various embodiments of a valve of the present invention. Generally, valve can be implanted within the fluid passageway of a body lumen, such as for replacement of a valve structure within the body lumen (e.g., a venous valve), to regulate the flow of a bodily fluid through the body lumen in a single direction. FIGS. 1A and 1B illustrate one embodiment of a venous valve 100. Venous valve 100 includes a tubular frame 102 and a cover 104 for the venous valve 100, where both the tubular frame 102 and the cover 104 can resiliently radially collapse and expand. The tubular frame 102 includes an outer surface 106 and an inner surface 108 opposite the outer surface 106. The inner surface 108 defines a lumen 110 of the venous valve 100 for passing fluid (e.g., blood) therethrough. The tubular frame 102 also includes a first end 112 and a second end 114.

In one embodiment, the cover 104 can be located over at least the outer surface 106 of the tubular frame 102. For example, the cover 104 can extend around a perimeter of the tubular frame 102 so as to completely cover the outer surface of the tubular frame 102. In other words, the cover 104 extends over the outer surface of the tubular frame 102 so that there are no exposed portions of the outer surface of the tubular frame 102. In an additional embodiment, the cover 104 can also be located over at least the inner surface 108 of the tubular frame 102. A further embodiment includes the cover 104 located over at least the outer surface 106 and the inner surface 108. The cover 104 can further include surfaces defining a reversibly sealable opening 116 for unidirectional flow of a liquid through the lumen 110. For example, the surfaces of the cover 104 can be deflectable between a closed configuration in which fluid flow through the lumen 110 can be restricted and an open configuration in which fluid flow through the lumen 110 can be permitted.

The tubular frame 102 can be formed from a wide variety of materials and in a wide variety of configurations. Generally, tubular frame 102 can have a unitary structure with an open frame configuration. For example, the open frame configuration can include frame members 117 that define openings 119 through the tubular frame 102. The tubular frame 102 can also be self-expanding. Examples of self-expanding frames include those formed from temperature-sensitive memory alloy which changes shape at a designated temperature or temperature range. Alternatively, the self-expanding frames can include those having a spring-bias. In addition, the tubular frame 102 can have a configuration that allows the frame 102 be radially expandable through the use of a balloon catheter.

Figure 1B:
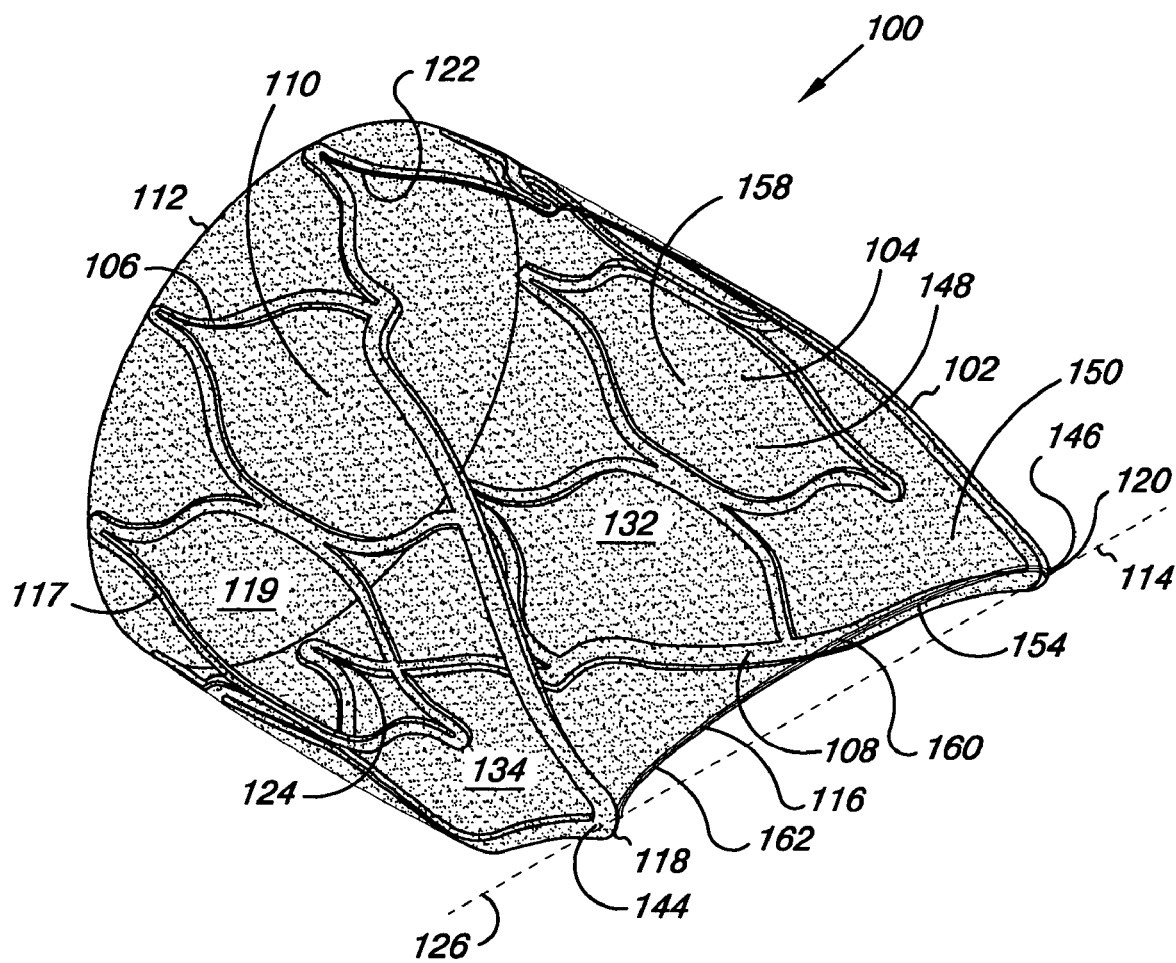

In one embodiment, the tubular frame 102 can include an open frame configuration that includes a first vertex 118 and a second vertex 120 relative the first end 112 of the tubular frame 102. Tubular frame 102 can further include a first valley 122 and a second valley 124 adjacent the first end 112 relative the first vertex 118 and the second vertex 120. As illustrated in FIGS. 1A and 1B, the first vertex 118 and the second vertex 120 can be positioned opposite each other along a common axis 126. FIGS. 1A and 1B also illustrate that the first valley 122 and the second valley 124 can be positioned opposite each other and perpendicular to axis 126. Other relative positions for the first and second vertex 118 and 120, and the first and second valley 122 and 124 are also possible.

Figure 2A:
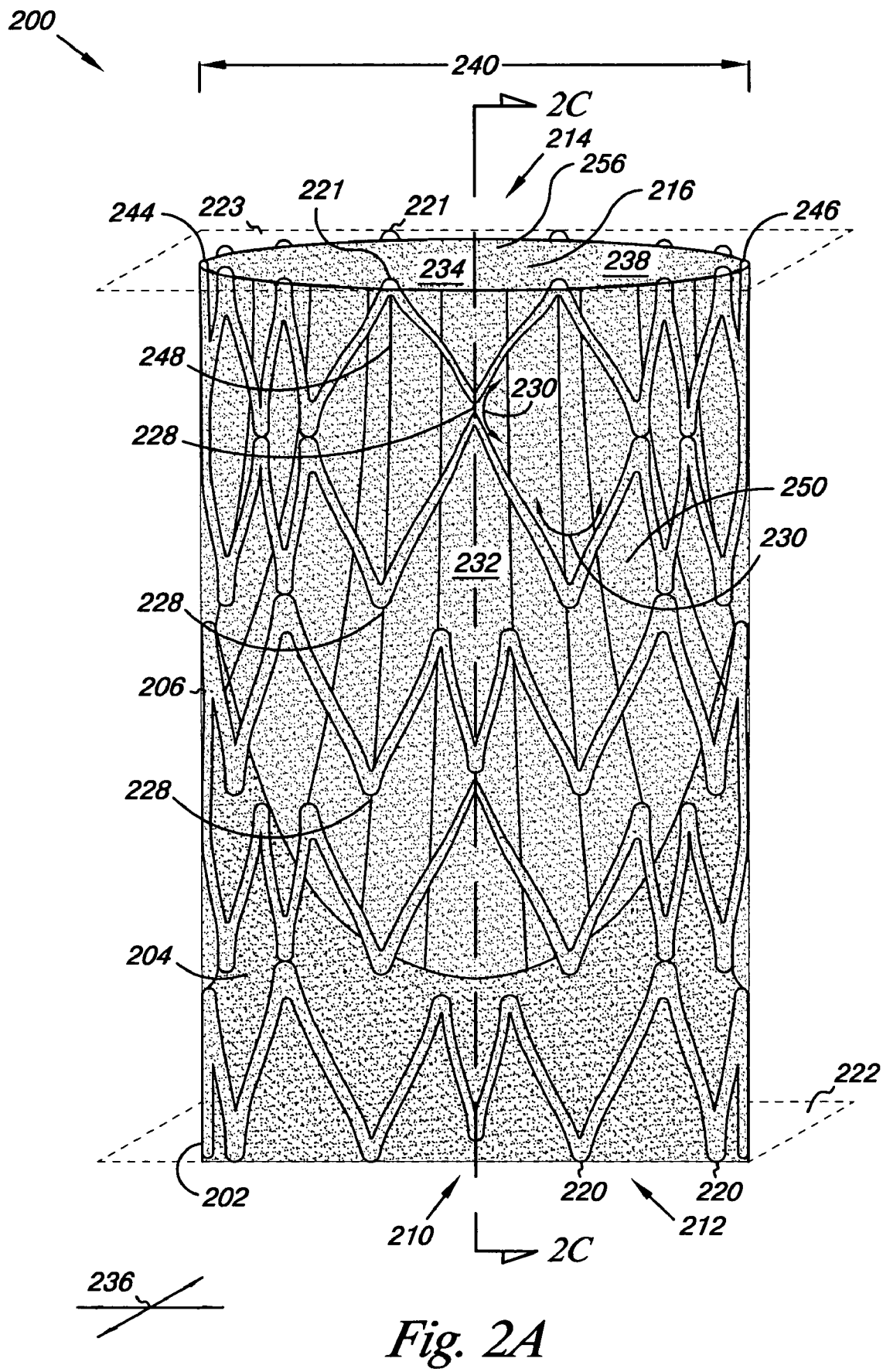
FIGS. 2A-2D illustrate an embodiment of a valve in perspective view (FIGS. 2A and 2B) and sectional view (FIGS. 2C and 2D) of the valve.
Figure 2B:
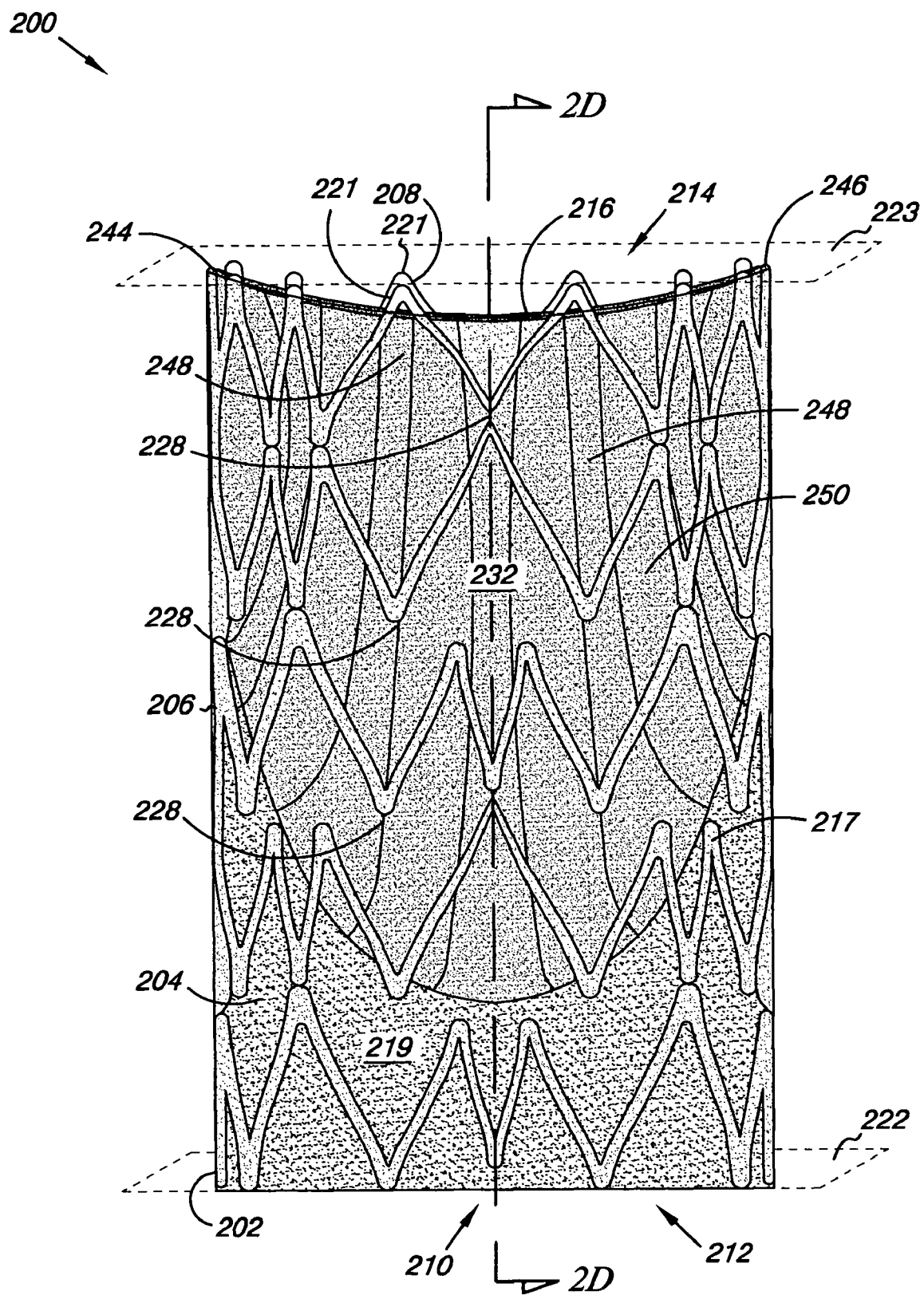
Figure 2C:
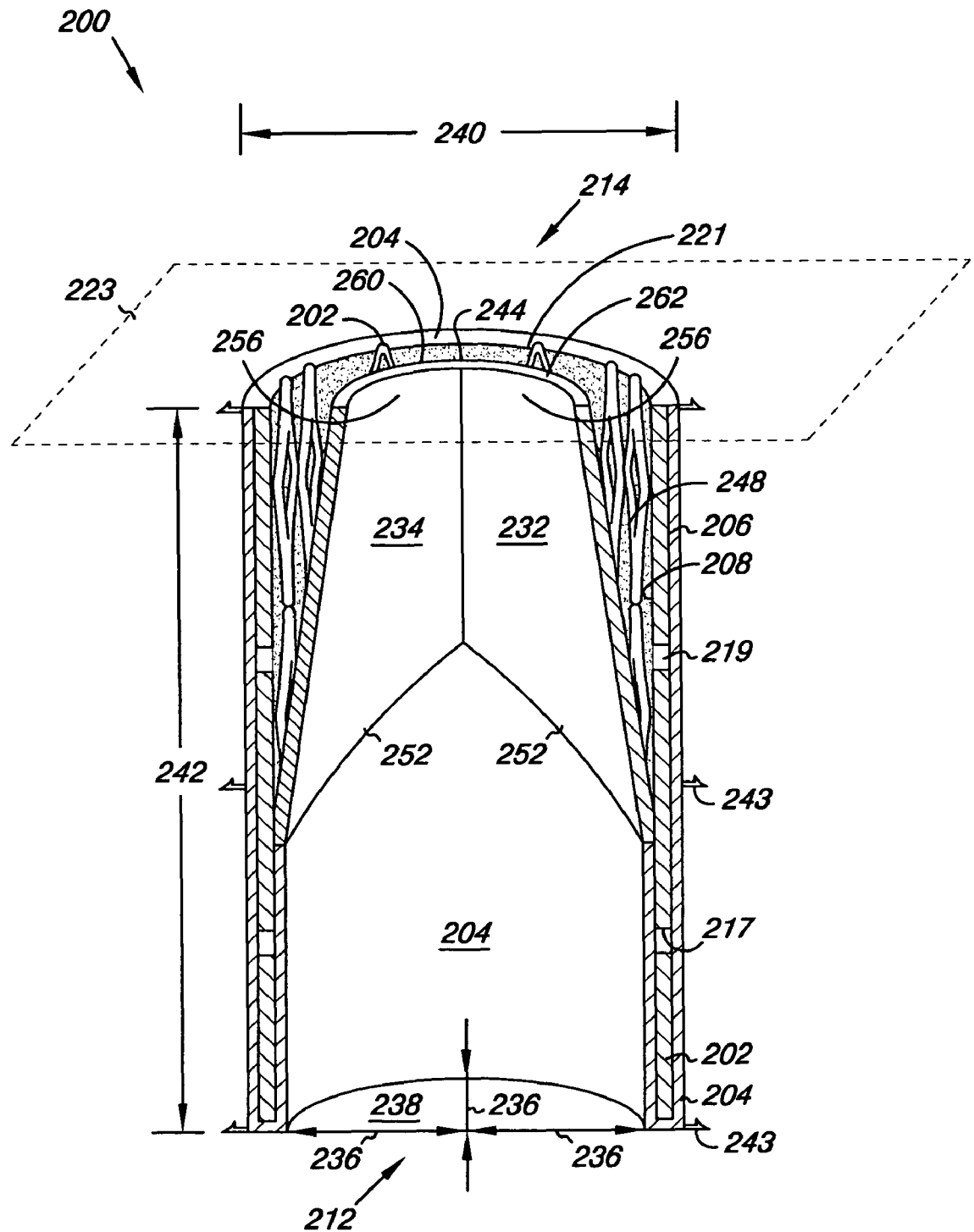
Figure 2D:
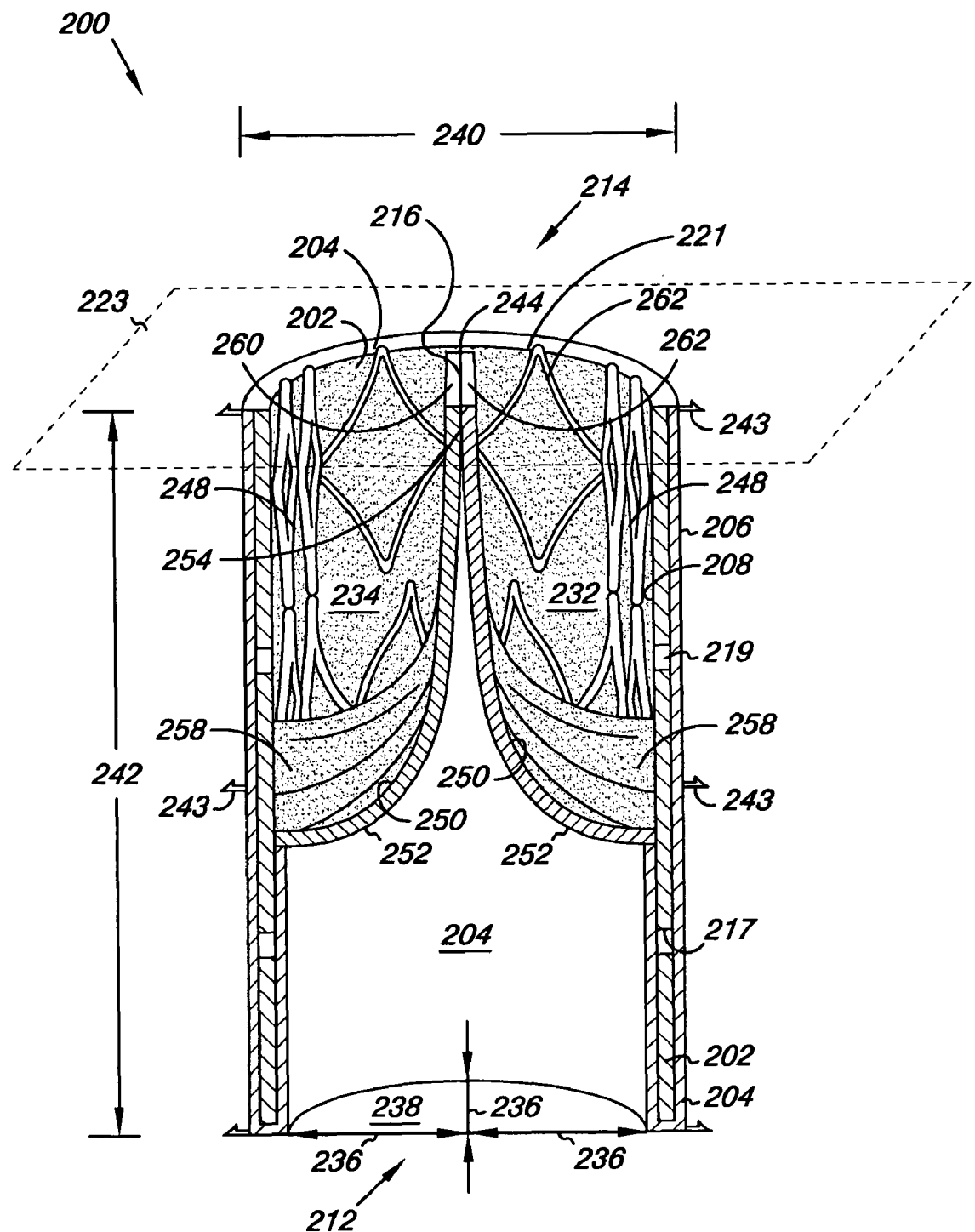

FIGS. 2A-2D illustrate an additional embodiment of a venous valve 200. FIGS. 2A and 2B provide a perspective illustration of valve 200 in an open configuration (FIG. 2A) and a closed configuration (FIG. 2B). FIGS. 2C and 2D provide a sectional view of FIGS. 2A and 2B, respectively, to more clearly illustrate the embodiment of the venous valve 200.

Venous valve 200 includes a tubular frame 202 and a cover 204 for the venous valve 200 where both the tubular frame 202 and the cover 204 can resiliently radially collapse and expand. The tubular frame 202 includes an outer surface 206 and an inner surface 208 opposite the outer surface 206. The inner surface 208 defines a lumen 210 of the venous valve 200 for passing fluid (e.g., blood) therethrough. The tubular frame 202 also includes a first end 212 and a second end 214.

In one embodiment, the cover 204 can be located over at least the outer surface 206 of the tubular frame 202. In an additional embodiment, the cover 204 can be located over at least the inner surface 208 of the tubular frame 202. A further embodiment includes the cover 204 located over at least the outer surface 206 and the inner surface 208. The cover 204 further includes surfaces defining a reversibly sealable opening 216 for unidirectional flow of a liquid through the lumen 210. For example, the surfaces of the cover 204 can be deflectable between a closed configuration in which fluid flow through the lumen 210 can be restricted and an open configuration in which fluid flow through the lumen 210 can be permitted.

Generally, tubular frame 202 can have a unitary structure with an open frame configuration. For example, the open frame configuration can include frame members 217 that define openings 219 through the tubular frame 202. The tubular frame 202 can include an open frame configuration in which the first end 212 and the second end 214 each include a plurality of end portions 221 that lay on a common plane 223. As illustrated in FIGS. 2A-2D, the plurality of end portions 221 that lay on the common plane 223. However, the plurality of end portions 221 need not all lay on the common plane 223 and 222. It is possible that one or more of the end portions 221 lay above and/or below the common plane 223.

While the tubular frame 102 and/or 202 illustrated herein is shown having a circular configuration, other configurations are also possible. For example, the tubular frame 102 and/or 202 can also include an elliptical configuration. As such, the present invention should not be limited to the illustration of the tubular frame 102 and/or 202.

The tubular frame 202 further includes elastic regions 228. Typically, the elastic regions 228 can occur at portions of the tubular frame 202 that include curves 230 in the frame members 217. The elastic regions 228 allow the valve 200 to accommodate changes in body lumen size (e.g., diameter of the body lumen) by flexing to expand and/or contract to change the diameter of the tubular frame 202. In one embodiment, the curves 230 in the frame members 217 can act as springs to allow the valve 200 to resiliently radially collapse and expand. The valve frame 202 can also provide sufficient contact and expansion force with the surface of a body lumen wall to encourage fixation of the valve 200 and to prevent retrograde flow within the body lumen. Anchoring elements (e.g., barbs) can also be included with valve 200, as will be discussed herein.

The elastic regions 228 of the valve frame 202 allow valve 200 to elastically and repeatably travel between a collapsed state and an expanded state. FIG. 3A provides an example of the valve 300 in a collapsed state, and FIG. 3B provides an example of the valve 300 in an expanded state. As shown in FIGS. 3A and 3B, the valve 300 can travel between the collapsed and the expanded state along a radial travel path 336, where there can be a change in a cross sectional area 338 of the lumen 310. For example, the valve frame 302 can travel along the radial travel path 336 so as to change a width 340 of lumen 310. This can allow the valve 300 to react appropriately to any distension and contraction of the lumen in which the valve 300 is placed.

In addition to the curves 230, the elastic regions 228 can further include, but are not limited to, other shapes for the valve frame 202 that allow for repeatable travel between the collapsed state and the expanded state. For example, the elastic regions 228 can include integrated springs having a circular or an elliptical coil configuration. Other shapes are also possible.

Frame member 217 of the valve frame 202 can include a variety of cross-sectional shapes and dimensions. For example, cross-sectional shapes for the frame member 217 can include, but are not limited to, circular, tubular, I-shaped, T-shaped, oval, trapezoidal, and triangular. The frame member 217 can also have a single cross-sectional shape (e.g., all of valve frame 202 can have a circular cross-sectional shape). In an additional embodiment, the frame member 217 can have two or more cross-sectional shapes (e.g., a circular cross-sectional shape in the elastic region 228 and a different cross-sectional shape in other regions of valve frame 202).

Valve frame 202 can also include one or more contiguous frame member 217. For example, the frame member 217 of valve frame 202 can be a single contiguous member. The single contiguous member can be bent around an elongate tubular mandrel to form the valve frame 202. The free ends of the single contiguous member can then be welded, fused, crimped, or otherwise joined together to form the valve frame 202. In an additional embodiment, the frame member 217 of valve frame 202 can be derived (e.g., laser cut, water cut) from a single tubular segment. In an alternative embodiment, methods of joining the frame member 217 to create the elastic region 228 include, but are not limited to, welding, gluing, and fusing the frame member 217. The valve frame 202 can be heat set by a method as is typically known for the material which forms the valve frame 202.

The valve frame 202 can be formed from any number of materials. For example, the valve frame 202 can be formed from a biocompatible metal, metal alloy, polymeric material, or combination thereof. As discussed herein, the valve frame 202 can be self-expanding or balloon expandable. In addition, the valve frame 202 can be configured so as to have the ability to move radially between the collapsed state and the expanded state. To accomplish this, the material used to form the valve frame 202 should exhibit a low elastic modulus and a high yield stress for large elastic strains that can recover from elastic deformations. Examples of suitable materials include, but are not limited to, medical grade stainless steel (e.g., 316L), titanium, tantalum, platinum alloys, niobium alloys, cobalt alloys, alginate, or combinations thereof. In an additional embodiment, the valve frame 202 may be formed from a shape-memory material, such as shape memory plastics, polymers, and thermoplastic materials which are inert in the body. Shaped memory alloys having superelastic properties generally made from specific ratios of nickel and titanium, commonly known as nitinol, are also possible materials. Other materials are also possible.

Tubular frame 202 can be expanded to provide lumen 210 having any number of sizes. For example, the size of lumen 210 can be determined based upon the type of body lumen and the body lumen size in which the valve 200 is to be placed. In an additional example, there can also be a minimum value for the width 240 for the tubular frame 202 that ensures that the tubular frame 202 will have an appropriate expansion force against the inner wall of the body lumen in which the valve 200 is being placed. The tubular frame 202 can also include a longitudinal length 242.

In one embodiment, the valve frame 202 can further include one or more anchoring elements. For example, the one or more anchoring elements can include, but are not limited to, one or more barbs 243 projecting from the outer surface 206 of the tubular frame 202. The valve 200 can further include one or more radiopaque markers (e.g., tabs, sleeves, welds). For example, one or more portions of the valve frame 202 can be formed from a radiopaque material. Radiopaque markers can be attached to and/or coated onto one or more locations along the valve frame 202. Examples of radiopaque material include, but are not limited to, gold, tantalum, and platinum. The position of the one or more radiopaque markers can be selected so as to provide information on the position, location and orientation of the valve 200 during its implantation.

As discussed herein, valve 100 further includes cover 104 having surfaces defining the reversibly sealable opening 116 for unidirectional flow of a liquid through the lumen 110. For the embodiment illustrated in FIGS. 1A and 1B, the cover 104 extends over at least a portion of the tubular frame 102 to a first connection point 144 and a second connection point 146 on the tubular frame 102. In one example, the first connection point 144 and the second connection point 146 can be located at the first vertex 118 and the second vertex 120 of the tubular frame 102. The cover 104 extends between the first connection point 144 and the second connection point 146 to provide a first valve leaflet 132 and a second valve leaflet 134. The first valve leaflet 132 and the second valve leaflet 134 can form the reversibly sealable opening 116 extending between the first connection point 144 and the second connection point 146. So, for the example shown in FIG. 1 the first valve leaflet 132 and the second valve leaflet 134 form the reversibly sealable opening 116 extending between the first vertex 118 and the second vertex 120 of the tubular frame 102.

As illustrated, the first valve leaflet 132 and the second valve leaflet 134 include a region 148 of the cover 104 that can move relative the tubular frame 102. The region 148 of the cover 104 can be unbound (i.e., unsupported) by the tubular frame 102 and extends between the first connection point 144 and the second connection point 146 of the valve 100. This configuration permits the reversibly sealable opening 116 to open and close in response to the fluid pressure differential across the valve leaflets 132 and 134.

For example, under antegrade fluid flow (i.e., positive fluid pressure) from the first end 112 towards the second end 114 of the valve 100, the first and second valve leaflets 132 and 134 can expand toward the inner surface 108 to create an opening through which fluid is permitted to move. In one example, the first valve leaflet 132 and the second valve leaflet 134 can each expand to define a semi-tubular structure when fluid opens the reversibly sealable opening 116. An example of the open configuration for the valve is shown in FIGS. 1A and 2A.

Under a retrograde fluid flow (i.e., negative fluid pressure) from the second end 114 towards the first end 112, the first and second valve leaflets 132 and 134 can move away from the inner surface 108 as the valve leaflets 132 and 134 begin to close valve 100. In one example, a pocket exists between the frame 102 and each of the first and second valve leaflets 132 and 134. The pocket allows fluid from the retrograde flow to develop pressure on a first major face 150 of the first and second valve leaflets 132 and 134. As fluid pressure develops, the first and second valve leaflets 132 and 134 collapse, closing the reversibly sealable opening 116 to create a seal 154, thereby restricting retrograde fluid flow through the valve 100. In one example, the seal 154 can be created by the joining of a sealing surface 156 of the first and second valve leaflets 132 and 134. In the closed configuration, the first and second valve leaflets 132 and 134 can each have a concave structure 158 when fluid closes the reversibly sealable opening 116. An example of the closed configuration for the valve is shown in FIGS. 1B and 2B.

Valve 100 provides an embodiment in which the surfaces defining the reversibly sealable opening 116 provide a bi-leaflet configuration (i.e., a bicuspid valve) for valve 100. Although the embodiments in FIGS. 1A-B and 2A-D illustrate and describe a bi-leaflet configuration for the valve of the present invention, designs employing a different number of valve leaflets (e.g., tri-leaflet valve) are possible. For example, additional connection points (e.g., three or more) could be used to provide additional valve leaflets (e.g., a tri-leaflet valve).

The first valve leaflet 132 and the second valve leaflet 134 can have a variety of sizes and shapes. For example, each of the first valve leaflet 132 and the second valve leaflet 134 can have a similar size and shape. In addition, each of the first valve leaflet 132 and the second valve leaflet 134 can include opposed first and second major surfaces 150 and 152, respectively. Each first major surface 150 of the first valve leaflet 132 and the second valve leaflet 134 can be oriented to face the second end 114 of valve 100.

Each of the first valve leaflet 132 and the second valve leaflet 134 can further provide the sealing surface 156 formed by portions of the first valve leaflet 132 and the second valve leaflet 134, where the sealing surface 156 can engage to define the closed configuration (FIG. 1B) of valve 100. Sealing surface 156 of the first valve leaflet 132 and the second valve leaflet 134 can separate to provide for an open configuration (FIG. 1A) of valve 100. In an additional example, each of the first valve leaflet 132 and the second valve leaflet 134 need not have a similar size and shape (i.e., the valve leaflets can have a different size and shape with respect to each other).

In one embodiment, each of the first valve leaflet 132 and the second valve leaflet 134 includes sufficient excess material spanning tubular frame 102 such that fluid pressure (e.g., antegrade flow) acting on the second major surface 152 of the first valve leaflet 132 and the second valve leaflet 134 forces the valve 100 into an open configuration (FIG. 1A). The first valve leaflet 132 and the second valve leaflet 134 further include arcuate edges 160 and 162 that are positioned adjacent each other along a substantially catenary curve between the connection point 144 and the second connection point 146 in the closed configuration (FIG. 1B) of valve 100. Similarly, arcuate edges 160 and 162 can define opening 116 when the valve 100 is in the open configuration (FIG. 1A).

In an additional embodiment, in the open configuration the portion of the cover 104 forming the first valve leaflet 132 and the second valve leaflet 134 provides sufficient excess material spanning between the connection point 144 and the second connection point 146 to allow the first and second major surfaces 150 and 152 to take on a semi-tubular structure 164, as shown in FIG. 1A, when fluid pressure opens the valve 100. In an additional embodiment, arcuate edge 160 and 162 of valve 100 can open to approximately the full inner diameter of a body lumen.

Each of the second major surfaces 152 of the first valve leaflet 132 and the second valve leaflet 134 can further include a curve imparted thereto so as to provide the second major surface 152 with the concave structure 158. The concave structure 158 allows the first valve leaflet 132 and the second valve leaflet 134 to better collect retrograde fluid flow to urge the first valve leaflet 132 and the second valve leaflet 134 towards the closed configuration. For example, as retrograde flow begins, the first valve leaflet 132 and the second valve leaflet 134 respond by moving towards the center of valve 100. As the first valve leaflet 132 and the second valve leaflet 134 approach the center of the device the sealing surfaces 156 make sufficient contact to effectively close valve 100 and restrict retrograde fluid flow.

In an additional embodiment, the first valve leaflet 132 and the second valve leaflet 134 can include one or more support structures, where the support structures can be integrated into and/or onto the valve leaflets 132 and 134. For example, the first valve leaflet 132 and the second valve leaflet 134 can include one or more support ribs having a predetermined shape. In one embodiment, the predetermined shape of the support ribs can include a curved bias so as to provide the first valve leaflet 132 and the second valve leaflet 134 with a curved configuration. Support ribs can be constructed of a flexible material and have dimensions (e.g., thickness, width and length) and cross-sectional shape that allows the support ribs to be flexible when the first valve leaflet 132 and the second valve leaflet 134 are urged into an open position, and stiff when the first valve leaflet 132 and the second valve leaflet 134 are urged into a closed position upon experiencing sufficient back flow pressure from the direction downstream from the valve. In an additional embodiment, support ribs can also be attached to valve frame 102 so as to impart a spring bias to the valve leaflets in either the open or the closed configuration.

In one embodiment, the material of the first valve leaflet 132 and the second valve leaflet 134 can be sufficiently thin and pliable so as to permit radially-collapsing of the valve leaflets for delivery by catheter to a location within a body lumen. The first valve leaflet 132 and the second valve leaflet 134 can be constructed of a fluid-impermeable biocompatible material that can be either synthetic or biologic. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), Dacron, polyethylene (PE), polyethylene terephthalate (PET), silk, urethane, Rayon, Silicone, or the like. Possible biologic materials include, but are not limited to, autologous, allogeneic or xenograft material. These include explanted veins and decellularized basement membrane materials, such as small intestine submucosa (SIS) or umbilical vein.

As discussed herein, the cover 104 can be located over at least the outer surface 106 of the tubular frame 102. FIGS. 1A and 1B illustrate this embodiment. In an additional embodiment, the cover 104 can also be located over at least the inner surface 108 of the tubular frame 102. FIGS. 2A-2D illustrate of this embodiment. In one example, the cover 104 can further be located over the openings 119 defined by the members 117 of the tubular frame 102. The cover 104 can also be joined to itself through the openings 119 so as to fully or partially encase the tubular frame 102. Numerous techniques may be employed to laminate or bond cover 104 on the outer surface 106 and/or the inner surface 108 of the tubular frame 102, including heat setting, adhesive welding, application of uniform force and other bonding techniques. Additionally, the cover 104 may be folded over the first end of the tubular frame 102 to provide the cover 104 on both the outer surface 106 and the inner surface 108. Cover 104 can also be joined to itself and/or the members 117 according to the methods described in U.S. Patent Application Publication US 2002/0178570 to Sogard et al., which is hereby incorporated by reference in its entirety.

The cover 104 can also be coupled to the connection points so as to form the valve leaflets, as discussed herein. In one embodiment, the cover 104 can be in the form of a sheet or a sleeve of material, as discussed herein, which can be connected to the tubular frame 102. Alternatively, the cover 104 can initially be in the form of a liquid that can be used to cast and/or form the cover over the tubular frame 102. Other forms, including intermediate forms, of the cover 104 are also possible.

The cover 104 can be coupled to the tubular frame 102, including the connection points 144 and 146, in a variety of ways so as to provide the various embodiments of the valve of the present invention. For example, a variety of fasteners can be used to couple the cover 104 to the tubular frame 102 so as to form the valve 100. Suitable fasteners can include, but are not limited to, biocompatible staples, glues, sutures or combinations thereof. In an additional embodiment, the cover 104 can be coupled to the tubular frame 102 through the use of heat sealing, solvent bonding, adhesive bonding, or welding cover 104 to either a portion of the cover 104 (i.e., itself) and/or the tubular frame 102.

The cover 104, including the valve leaflets 132 and 134, may also be treated and/or coated with any number of surface or material treatments. For example, the cover 104 can be treated with one or more biologically active compounds and/or materials that may promote and/or inhibit endothelization and/or smooth muscle cell growth of the cover 104, including the valve leaflets 132 and 134. Similarly, the cover 104 may be seeded and covered with cultured tissue cells (e.g., endothelial cells) derived from a either a donor or the host patient which are attached to the valve leaflets 132 and 134. The cultured tissue cells may be initially positioned to extend either partially or fully over the valve leaflets 132 and 134.

Cover 104, in addition to forming valve leaflets 132 and 134, can also be capable of inhibiting thrombus formation. Additionally, cover 104 may either prevent or facilitate tissue ingrowth therethrough, as the particular application for the valve 100 may dictate. For example, cover 104 on the outer surface 106 may be formed from a porous material to facilitate tissue ingrowth therethrough, while cover 104 on the inner surface 108 may be formed from a material or a treated material which inhibits tissue ingrowth.

The embodiments of the valve of the present invention can be formed in any number of ways. For example, FIGS. 4A-4D provide an illustration of a method for forming valve 400. FIG. 4A illustrates one embodiment of cover 404 having a tubular configuration that includes a symmetrical portion 466 and a tapering portion 468. In the present example, the cover 404 can be formed from a continuous piece of tubular material. In one example, the tapering portion 468 can be formed by removing predetermined portions of the tubular material from the continuous piece of tubular material.

For example, FIGS. 5A-5C illustrate one embodiment of creating a tapering portion 568 for the cover 504. Cover 504 is shown in a flattened configuration to better illustrate forming the tapering portion 568 according to the present embodiment. As FIG. 5A illustrates, cover 504 can have an initial symmetrical configuration. FIG. 5A also illustrates that a portion 569, defined by line 570, of the cover 504 in the symmetrical configuration for removal in forming the tapering portion. FIG. 5B shows the portion 569 removed from the cover 504. Once removed, the cover 504 includes edges 571 that are joined to form the tapering portion 568. FIG. 5C provides an example of edges 571 joined for the tapering portion 568. In one example, the edges 571 can be joined in any number of ways, including any of those recited herein.

Other ways of forming the tapering portion 468 during the manufacturing of the cover 404 also exist. For example, the cover 404 can be cast, extruded, or molded (including blow molded) to form the tapering portion 468. In addition, tapering portion 468 can be provided separately from the symmetrical portion 466. In other words, each portion (e.g., tapering portion 468 and the symmetrical portion 466) are separate pieces that can either be then be joined, by method described herein, or used separately in forming valve 400.

In an alternative embodiment, the tapering portion 468 can be created as a result of at least a portion of the cover 404 being stretched over the tubular frame 402. For example, the cover 404 can have a cylindrical shape of essentially uniform inner diameter, where the inner diameter is less than an outer diameter of the tubular frame 402. The cover 404 can be stretched over the outer surface 406 of the tubular frame 402 such that the tapering portion 468 results as the cover 404 transitions from its stretched portion over the tubular frame 402 to the unstretched portion of the cover 404.

Referring again to FIGS. 4B-4D, the symmetrical portion 466 of the cover 404 can be placed around the outer surface 406 of the tubular frame 402. For example, the cover 404 can stretched slightly to allow the tubular frame 402 to be placed within the symmetrical portion 466 of the cover 404. Alternatively, the outer diameter of the tubular frame 402 could be enlarged so as to place the symmetrical portion 466 of the cover 404 around the outer surface 406 of the tubular frame 402. Other ways of placing the symmetrical portion 466 of the cover 404 around the outer surface 406 of the tubular frame 402 are also possible.

As FIG. 4C illustrates, a free end 472 of the tapering portion 468 can be folded and drawn into the lumen 410 of the tubular frame 402. The free end 472 is advanced toward the second end 414, so that the cover 404 extends over at least a portion of the inner surface 408 of the tubular frame 402. The free end 472 of the cover 404 can extend over at least the portion of the inner surface 408 to at least a first connection point 444 and a second connection point 446 on the tubular frame 402. As FIG. 4D illustrates, the cover 404 can be attached at the first connection point 444 and the second connection point 446 to form the first valve leaflet 432 and the second valve leaflet 434. As discussed herein, the first valve leaflet 432 and the second valve leaflet 434 include sealing surfaces 456 defining the reversibly sealable opening 416 for unidirectional flow of liquid through the lumen 410.

FIG. 4D further illustrates the cover 404 located over the outer surface 406 may be affixed to the cover 404 over at least a portion of the inner surface 408 through the openings 419 and/or affixed to the members 417 of the tubular frame 402. In addition, the cover 404 located over the outer surface 406 may be affixed at least to the members 417 of the tubular frame 402.

FIG. 6A-6E provides an alternative embodiment of forming a valve 600. In the present embodiment, the cover 604 can include at least two separate portions (e.g., symmetrical portion 666 shown in FIG. 6A and tapering portion 668 shown in FIG. 6B) that are affixed to the tubular frame 602 to form the valve 600. For example, the cover 604 can be formed from a symmetrical portion 666, shown in FIG. 6A, that is separate from a tapering portion 668, shown in FIG. 6B.

Figure 6C:
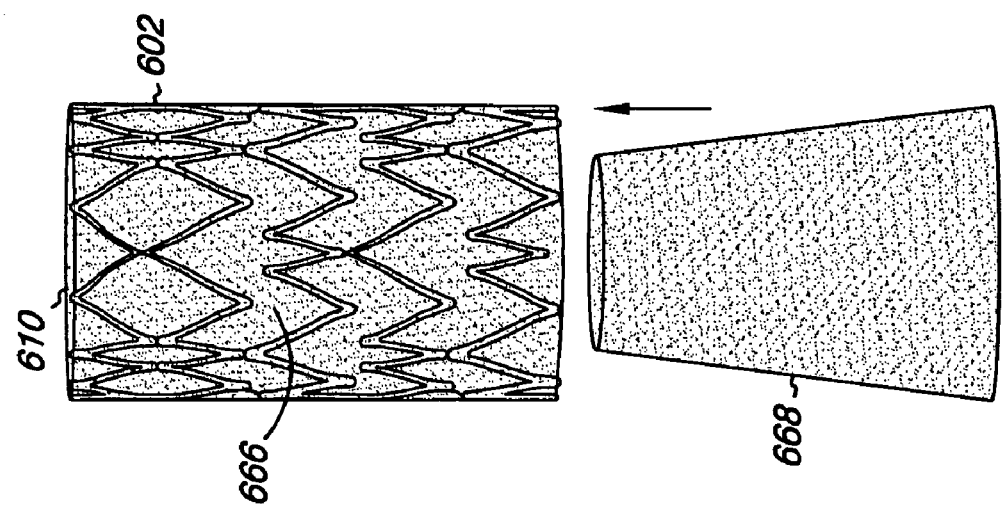
Figure 6B:
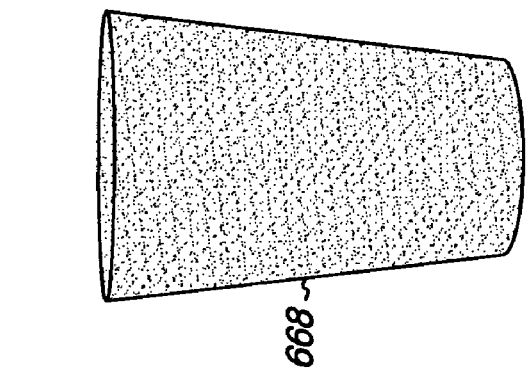
Figure 6A:
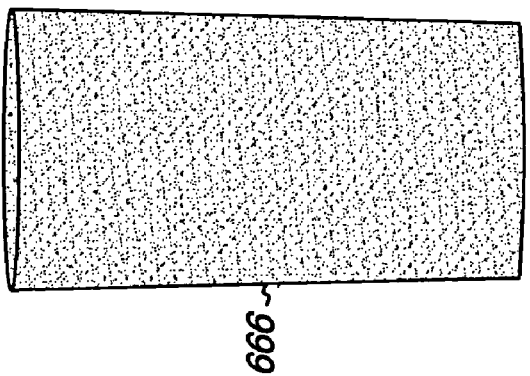
Figure 6D:
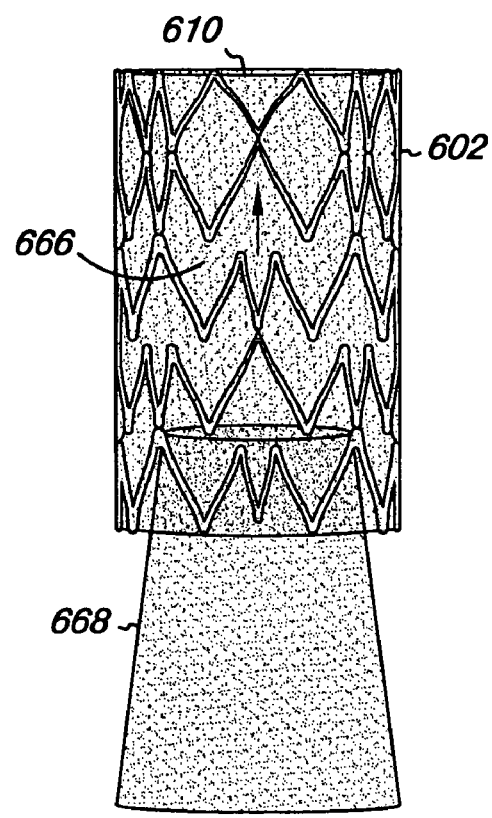
Figure 6E:
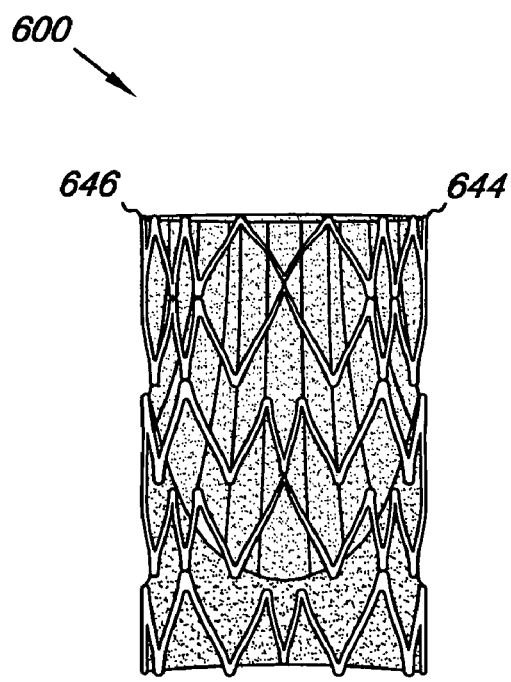

The tapering portion 668 and the symmetrical portion 666 can be affixed to the tubular frame 602 and to each other, as described herein, so as to form valve 600. For example, FIGS. 6C-6D illustrate symmetrical portion 666 affixed to tubular frame 602, with tapering portion 668 being inserted into lumen 610. FIG. 6E illustrates valve 600 upon affixing the tapering portion 668 to the symmetrical portion 666, the tubular frame 602 and the first and second connection points 644 and 646.

Figure 7A:
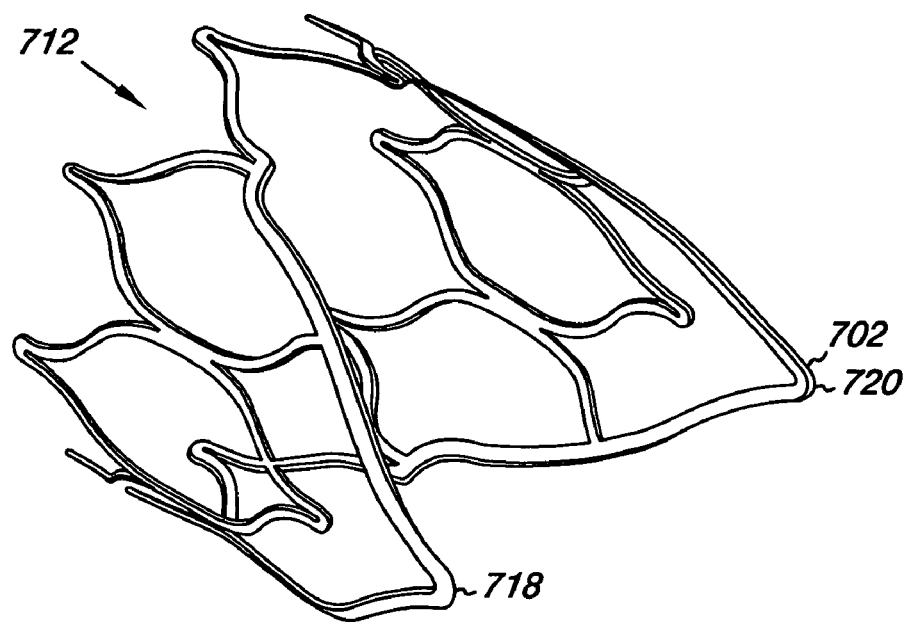
FIGS. 7A-7D illustrate an embodiment of forming a valve.
Figure 7B:
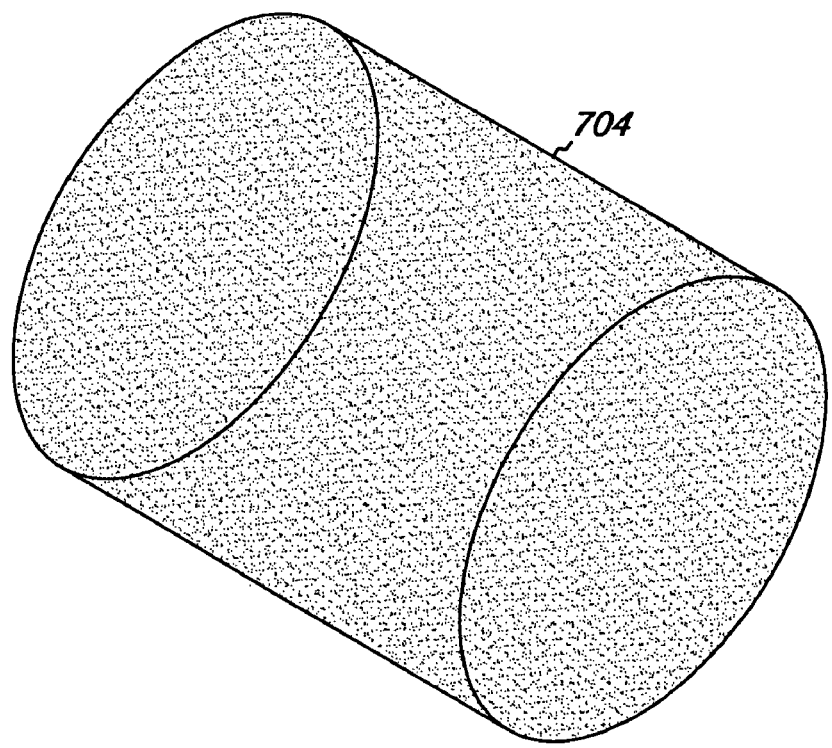
Figure 7C:
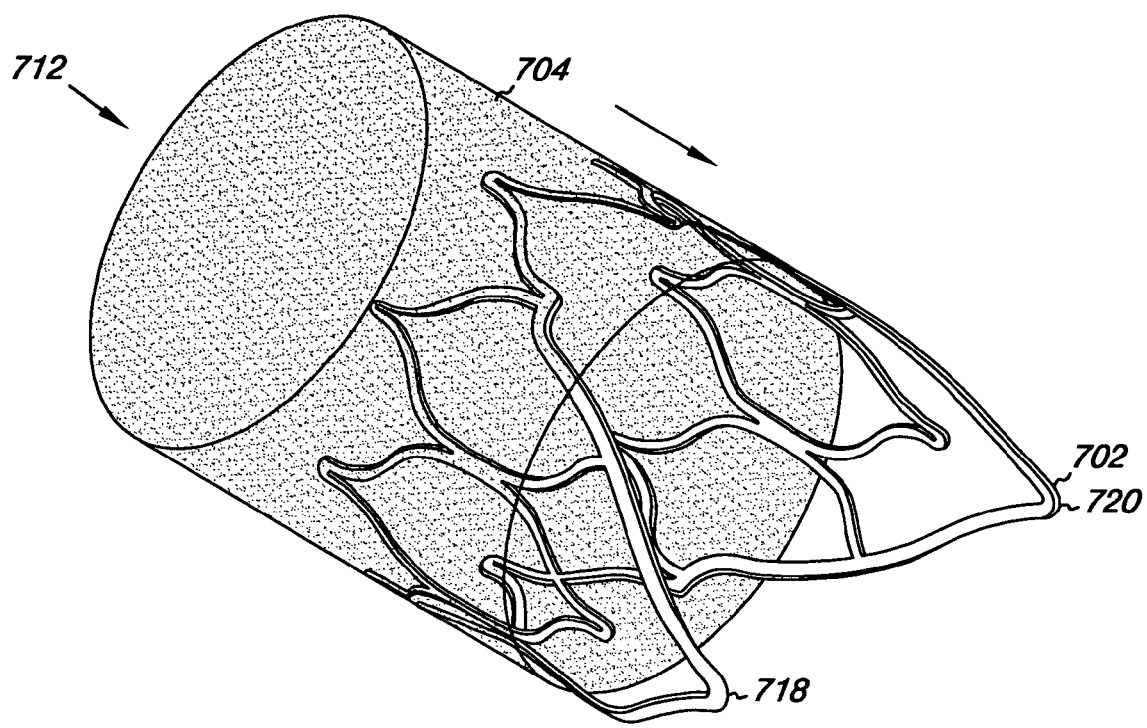
Figure 7D:
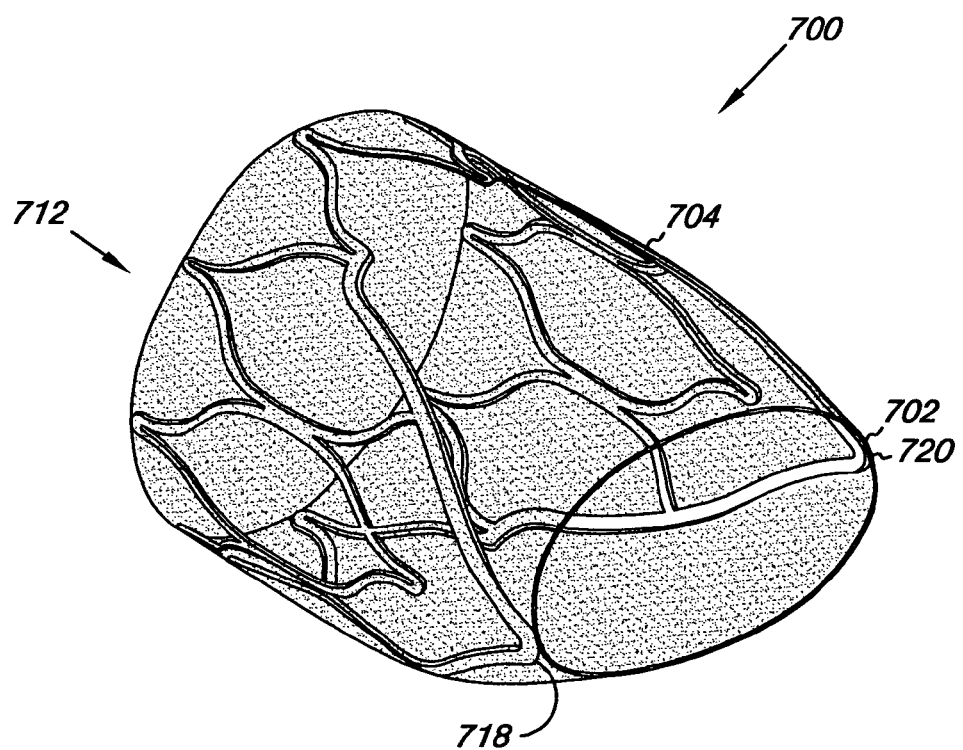

FIGS. 7A-7D illustrate an additional embodiment of forming a valve 700 according to the present invention. The valve 700 includes tubular frame 702 (FIG. 7A) and cover 704 (FIG. 7B). As discussed herein, tubular frame 702 has an open frame configuration that includes the first vertex 718 and a second vertex 720 relative the first end 712 of the tubular frame 702. In the present example, the cover 704 can have a tubular configuration, where the cover 704 can be positioned around and affixed to the tubular frame 702 (FIGS. 7C-7D) so as to form valve 700. For example, cover 704 and/or tubular frame 702 can be stretched so as to affix the cover 704 and the tubular frame 702. In addition, the cover 704 can be affixed to the tubular frame 702 by additional mechanical and/or chemical approaches, as discussed herein.

FIG. 8 illustrates one embodiment of a system 882. System 882 includes valve 800, as described herein, reversibly joined to catheter 874. The catheter 874 includes an elongate body 876 having a proximal end 878 and a distal end 879, where valve 800 can be located between the proximal end 878 and distal end 879. The catheter 874 can further include a lumen 880 longitudinally extending to the distal end 879. In one embodiment, lumen 880 extends between proximal end 878 and distal end 879 of catheter 874. The catheter 874 can further include a guidewire lumen 881 that extends within the elongate body 876, where the guidewire lumen 881 can receive a guidewire for positioning the catheter 874 and the valve 800 within a body lumen (e.g., a vein of a patient).

The system 882 can further include a deployment shaft 883 positioned within lumen 880, and a sheath 884 positioned adjacent the distal end 879. In one embodiment, the valve 800 can be positioned at least partially within the sheath 884 and adjacent the deployment shaft 883. The deployment shaft 883 can be moved within the lumen 880 to deploy valve 800. For example, deployment shaft 883 can be used to push valve 800 from sheath 884 in deploying valve 800.

FIG. 9 illustrates an additional embodiment of the system 982. The catheter 974 includes elongate body 976, lumen 980, a retraction system 986 and a retractable sheath 987. The retractable sheath 987 can be positioned over at least a portion of the elongate body 976, where the retractable sheath 987 can move longitudinally along the elongate body 976. The valve 900 can be positioned at least partially within the retractable sheath 987, where the retractable sheath 987 moves along the elongate body 976 to deploy the valve 900. In one embodiment, retraction system 986 includes one or more wires coupled to the retractable sheath 987, where the wires are positioned at least partially within and extend through lumen 980 in the elongate body 976. Wires of the retraction system 986 can then be used to retract the retractable sheath 987 in deploying valve 900.

Figure 10:
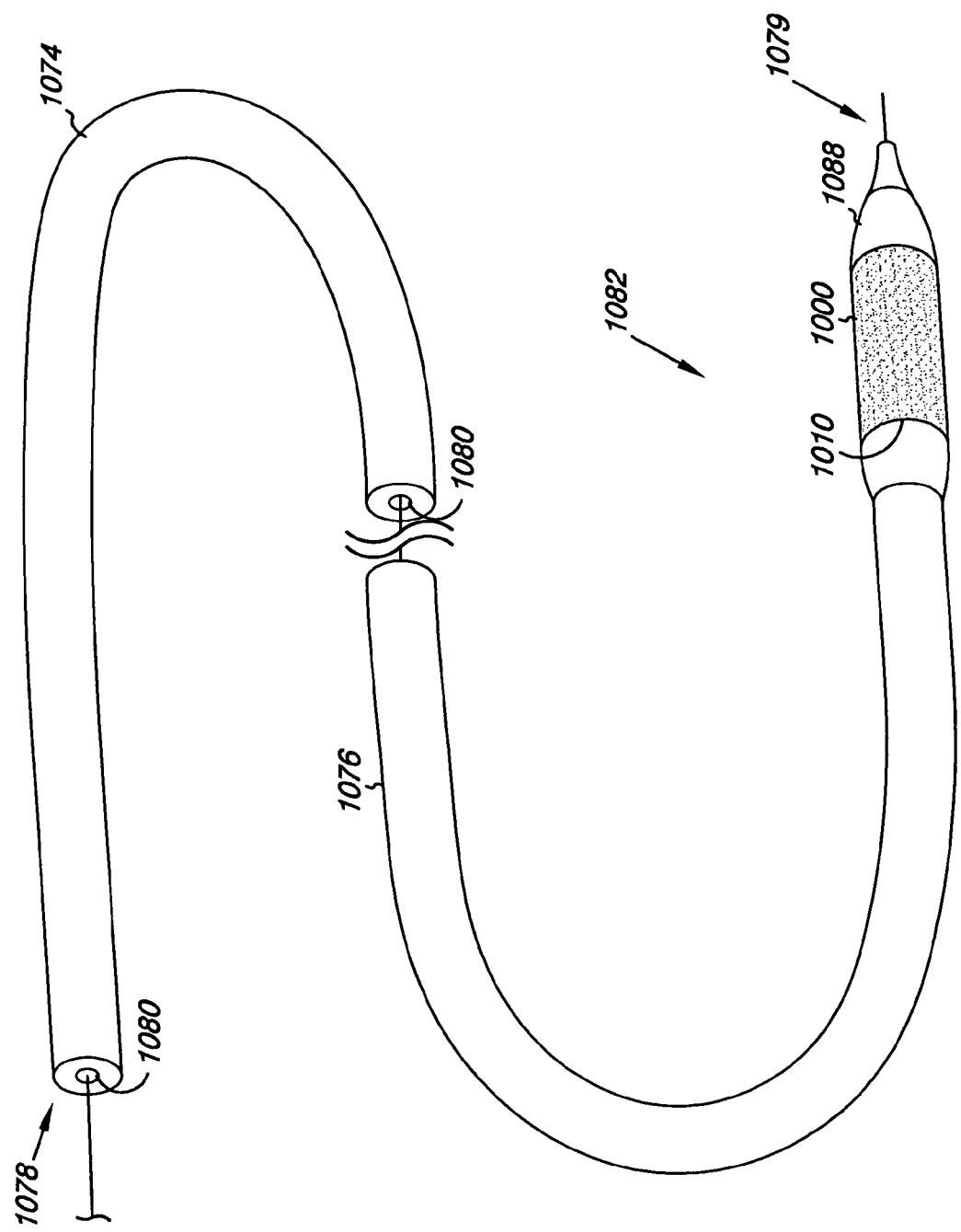
FIG. 10 illustrates an embodiment of a system that includes a valve.

FIG. 10 illustrates an additional embodiment of the system 1082. The catheter 1074 includes elongate body 1076, an inflatable balloon 1088 positioned adjacent the distal end 1079, and a lumen 1080 longitudinally extending in the elongate body 1076 of the catheter 1074 from the inflatable balloon 1088 to the proximal end 1078. In the present example, the inflatable balloon 1088 can be at least partially positioned within the lumen 1010 of the valve 1000. The inflatable balloon 1088 can be inflated through the lumen 1080 to deploy the valve 1000.

The embodiments of the present invention further include methods for forming the valve of the present invention, as discussed herein. For example, the valve can be formed from the tubular frame and the cover over at least the outer surface of the tubular frame, where the cover includes surfaces defining the reversibly sealable opening for unidirectional flow of a liquid through the lumen. In an additional example, the valve can be reversibly joined to the catheter, which can include a process of altering the shape of the valve from a first shape, for example an expanded state, to the compressed state, as described herein.

For example, the valve can be reversibly joined with the catheter by positioning valve in the compressed state at least partially within the sheath of the catheter. In one embodiment, positioning the valve at least partially within the sheath of the catheter includes positioning the valve in the compressed state adjacent the deployment shaft of the catheter. In an another embodiment, the sheath of the catheter functions as a retractable sheath, where the valve in the compressed state can be reversibly joined with the catheter by positioning the valve at least partially within the reversible sheath of the catheter. In a further embodiment, the catheter can include an inflatable balloon, where the balloon can be positioned at least partially within the lumen of the valve, for example, in its compressed state.

The embodiments of the valve described herein may be used to replace, supplement, or augment valve structures within one or more lumens of the body. For example, embodiments of the present invention may be used to replace an incompetent venous valve and help to decrease backflow of blood in the venous system of the legs.

In one embodiment, the method of replacing, supplementing, and/or augmenting a valve structure can include positioning at least part of the catheter including the valve at a predetermined location within the lumen of a body. For example, the predetermined location can include a position within a body lumen of a venous system of a patient, such as a vein of a leg.

In one embodiment, positioning the catheter that includes the valve within the body lumen of a venous system includes introducing the catheter into the venous system of the patient using minimally invasive percutaneous, transluminal catheter based delivery system, as is known in the art. For example, a guidewire can be positioned within a body lumen of a patient that includes the predetermined location. The catheter, including valve, as described herein, can be positioned over the guidewire and the catheter advanced so as to position the valve at or adjacent the predetermined location. In one embodiment, radiopaque markers on the catheter and/or the valve, as described herein, can be used to help locate and position the valve.

The valve can be deployed from the catheter at the predetermined location in any number of ways, as described herein. In one embodiment, valve of the present invention can be deployed and placed in any number of vascular locations. For example, valve can be deployed and placed within a major vein of a patient's leg. In one embodiment, major veins include, but are not limited to, those of the peripheral venous system. Examples of veins in the peripheral venous system include, but are not limited to, the superficial veins such as the short saphenous vein and the greater saphenous vein, and the veins of the deep venous system, such as the popliteal vein and the femoral vein.

As discussed herein, the valve can be deployed from the catheter in any number of ways. For example, the catheter can include the retractable sheath in which valve can be at least partially housed, as discussed herein. Valve can be deployed by retracting the retractable sheath of the catheter, where the valve self-expands to be positioned at the predetermined location. In an additional example, the catheter can include a deployment shaft and sheath in which valve can be at least partially housed adjacent the deployment shaft, as discussed herein. Valve can be deployed by moving the deployment shaft through the catheter to deploy valve from the sheath, where the valve self-expands to be positioned at the predetermined location. In an additional embodiment, the valve can be deployed through the use of an inflatable balloon.

Once implanted, the valve can provide sufficient contact and expansion force against the body lumen wall to prevent retrograde flow between the valve and the body lumen wall. For example, the valve can be selected to have a larger expansion diameter than the diameter of the inner wall of the body lumen. This can then allow valve to exert a force on the body lumen wall and accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

While the present invention has been shown and described in detail above, it will be clear to the person skilled in the art that changes and modifications may be made without departing from the spirit and scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the tubular frame 102 and/or the cover 104 can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A venous valve, comprising:
  a radially collapsible and expandable tubular frame with an open frame configuration, wherein the tubular frame includes an outer surface and an inner surface opposite the outer surface and defining a lumen, only one band of wishbone-shaped frame members, the band of wishbone-shaped frame members formed about a first end of the frame, and a first vertex and a second vertex relative the first end of the tubular frame, a first valley and a second valley extending from the first vertex and the second vertex to the first end of the tubular frame,
  wherein the first vertex and the second vertex are positioned opposite one another along a common axis, and
  wherein the first valley and the second valley are positioned opposite one another and are perpendicular to the common axis, and
  wherein, a first strut of the tubular frame passes immediately from the first vertex to the first valley and a second strut of the tubular frame passes immediately from the first valley to the second vertex to form a tapering point, and wherein each of the first strut and the second strut comprise a half-wishbone shape; and a radially collapsible and expandable tubular cover positioned around the entire outer surface of the tubular frame, wherein the tubular cover is connected to the first vertex and to the second vertex to form a first valve leaflet across the first valley and a second valve leaflet across the second valley between the first vertex and the second vertex to oppose flow of a liquid through the lumen from the second end to the first end.

2. The venous valve of claim 1, wherein the first valve leaflet and the second valve leaflet include arcuate edges at one end of the tubular cover to define a reversibly sealable opening extending between the first vertex and the second vertex.

3. The venous valve of claim 1, further including the cover over the inner surface of the tubular frame, wherein the cover over the inner surface extends to at least a first connection point and a second connection point on the tubular frame to form a first valve leaflet and a second valve leaflet.

4. The venous valve of claim 3, wherein the first valve leaflet and the second valve leaflet form the reversibly sealable opening extending between the first connection point and the second connection point.

5. A venous valve, comprising:
a radially collapsible and expandable tubular frame with an open frame configuration including only one band of wishbone-shaped frame members, the band of wishbone-shaped frame members formed about a first end of the frame, a first vertex and a second vertex relative the first end of the tubular frame, wherein the first vertex and the second vertex are positioned opposite each other along a common axis, a first valley and a second valley extending from the first vertex and the second vertex to the first end of the tubular frame, and wherein the first valley and the second valley are positioned opposite each other and are perpendicular to the common axis, and wherein the tubular frame includes an outer surface and an inner surface opposite the outer surface and defining a lumen, and a first strut of the tubular frame passes immediately from the first vertex to the first valley and a second strut of the tubular frame passes immediately from the first valley to the second vertex to form a tapering point, and wherein each of the first strut and the second strut comprise a half-wishbone shape; and a radially collapsible and expandable tubular cover extending over the entire outer surface of the tubular frame and connected to the first vertex and the second vertex to form a first valve leaflet and a second valve leaflet therebetween, wherein the first valve leaflet and the second valve leaflet reversibly transition between an open position and a closed position opposing flow of a liquid in one direction through the lumen.

6. The venous valve of claim 5, wherein the first valve leaflet and the second valve leaflet form a reversibly sealable opening extending between the first vertex and the second vertex.

7. The venous valve of claim 5, wherein the tubular frame and the tubular cover move between a collapsed state and an expanded state.

8. The venous valve of claim 5, wherein the first valve leaflet and the second valve leaflet include arcuate edges between the first vertex and the second vertex.

9. A system, comprising:
a venous valve, wherein the venous valve includes:
a radially collapsible and expandable tubular frame with an open frame configuration, wherein the tubular frame includes an outer surface and an inner surface opposite the outer surface and defining a lumen, only one band of wishbone-shaped frame members, the band of wishbone-shaped frame members formed about a first end of the frame, the frame having a first vertex and a second vertex relative the first end of the tubular frame, wherein the first vertex and the second vertex are positioned opposite each other along a common axis, and having a first valley and a second valley extending from the first vertex and the second vertex to the first end of the tubular frame, wherein the first valley and the second valley are positioned opposite each other and are perpendicular to the common axis and a first strut of the tubular frame passes immediately from the first vertex to the first valley and a second strut of the tubular frame passes immediately from the first valley to the second vertex to form a tapering point, and wherein each of the first strut and the second strut comprise a half-wishbone shape;

a radially collapsible and expandable tubular cover that extends over at least the entire outer surface of the tubular frame and is connected to the first vertex and the second vertex on the tubular frame to form a first valve leaflet and a second valve leaflet between the first vertex and the second vertex, where the first valve leaflet and the second valve leaflet reversibly transition between an open position and a closed position opposing flow of a liquid from the first end through the lumen; and a catheter including a proximal end and a distal end, the venous valve located between the proximal end and distal end of the catheter.

10. The system of claim 9, wherein the catheter includes an elongate body having a lumen longitudinally extending to the distal end, a deployment shaft positioned within the lumen, and a sheath positioned adjacent the distal end, the venous valve positioned at least partially within the sheath and adjacent the deployment shaft, wherein the deployment shaft moves within the lumen to deploy the venous valve.

11. The system of claim 9, wherein the catheter includes an elongate body and a retractable sheath over at least a portion of the elongate body, the venous valve positioned at least partially within the retractable sheath, wherein the retractable sheath moves along the elongate body to deploy the venous valve.

12. The system of claim 9, wherein the catheter includes an inflatable balloon positioned adjacent the distal end and a catheter lumen longitudinally extending in an elongate body of the catheter from the inflatable balloon to the distal end, the inflatable balloon at least partially positioned within the lumen of the venous valve, where the inflatable balloon inflates to deploy the venous valve.

13. The system of claim 9, wherein the tubular cover extends to at least the first vertex and the second vertex to form a first valve leaflet and a second valve leaflet between the first vertex and the second vertex, wherein the first valve leaflet and the second valve leaflet includes a surface defining a reversibly sealable opening for unidirectional flow of a liquid through the lumen.

14. The system of claim 9, wherein the cover extends over at least a portion of the inner surface of the tubular frame, wherein the cover over the at least the portion of the inner surface extends to at least a first connection point and a second connection point on the tubular frame to form a first valve leaflet and a second valve leaflet, wherein the first valve leaflet and the second valve leaflet includes a surface defining a reversibly sealable opening for unidirectional flow of a liquid through the lumen.

* * * * *